US012369579B2

(12) United States Patent
Jones, Jr. et al.

(10) Patent No.: US 12,369,579 B2
(45) Date of Patent: Jul. 29, 2025

(54) ANTIMICROBIAL AGENTS AND COMPOSITIONS AND USES THEREOF

(71) Applicant: KODA Therapeutics, LLC, West Bridgewater, MA (US)

(72) Inventors: Gerald S. Jones, Jr., Norwood, MA (US); Joseph P. St. Laurent, Lakeville, MA (US); Scott A. Goodrich, Stoughton, MA (US)

(73) Assignee: Koda Therapeutics, LLC, West Bridgewater, MA (US)

( * ) Notice: Subject to any disclaimer, the term of this patent is extended or adjusted under 35 U.S.C. 154(b) by 546 days.

(21) Appl. No.: 17/696,133

(22) Filed: Mar. 16, 2022

(65) Prior Publication Data

US 2022/0378044 A1    Dec. 1, 2022

Related U.S. Application Data

(63) Continuation of application No. PCT/US2020/051114, filed on Sep. 16, 2020.

(60) Provisional application No. 62/901,127, filed on Sep. 16, 2019, provisional application No. 62/901,126, filed on Sep. 16, 2019.

(51) Int. Cl.
| | |
|---|---|
| *A01N 43/08* | (2006.01) |
| *A01N 43/12* | (2006.01) |
| *A01N 43/30* | (2006.01) |
| *A01N 43/78* | (2006.01) |
| *A01N 57/10* | (2006.01) |

(52) U.S. Cl.
CPC ............. *A01N 43/08* (2013.01); *A01N 43/12* (2013.01); *A01N 43/30* (2013.01); *A01N 43/78* (2013.01); *A01N 57/10* (2013.01)

(58) Field of Classification Search
CPC .... A61P 31/04; A61P 1/04; A61P 1/00; A61P 43/00; A61P 1/10; A61P 1/14; A61P 11/06; A61P 25/02; A61P 31/00; A61P 31/14; A61P 31/16; A61P 1/16; A61P 13/12; A61P 29/00; A61P 7/10; A61P 9/04; A61P 9/12; A61P 17/02; A61P 17/10
See application file for complete search history.

(56) References Cited

U.S. PATENT DOCUMENTS

| | | |
|---|---|---|
| 4,115,415 A | 9/1978 | Yoshihara et al. |
| 7,186,272 B2 | 3/2007 | Heller |
| 7,544,366 B1 | 6/2009 | Lutz et al. |
| 2002/0082267 A1 | 6/2002 | Gerusz et al. |
| 2004/0014749 A1 | 1/2004 | Michaelis et al. |
| 2005/0202079 A1 | 9/2005 | Bielski et al. |
| 2015/0376413 A1 | 12/2015 | Higashi et al. |

FOREIGN PATENT DOCUMENTS

| | | |
|---|---|---|
| FR | 2325369 A1 | 4/1977 |
| WO | WO-1992/014458 A1 | 9/1992 |
| WO | 2001011966 A1 | 2/2001 |
| WO | 2001012604 A1 | 2/2001 |
| WO | 2010132515 A1 | 11/2010 |
| WO | 2014018571 A2 | 1/2014 |
| WO | 2021055506 A1 | 3/2021 |

OTHER PUBLICATIONS

Jones Jr et al., Antibacterial Organophosphorus Compounds: Phosphoranilidohydrazones of 5-Nitro-2-furaldehyde, Journal of Pharmaceutical Sciences, vol. 82, No. 7, Jul. 1993, pp. 755-757.
International Search Report and Written Opinion for PCT Application No. PCT/US2020/051114, mailed on Feb. 8, 2021, 18 pages.
Konigsberger et al. The synthesis of (R)- and (S)-alpha-trifluoromethyl-alpha-hydroxycarboxylic acids via enzymatic resolutions. Tetrahedron: Asymmetry 10 (1999) 679-687.
International Search Report and Written Opinion mailed Feb. 1, 2012, for International Application No. PCT/US2011/051960 filed Sep. 16, 2011 (6 pages).
Bagrov, F.V., Matveeva, "Phosphorus-containing hydrazones as additives for lubricating greases" T.M. & Petrukhin, V. A. Chem Technol Fuels Oils (1997) vol. 33: p. 41-43.
Bachelet et al. "Research on Nitrate Derivatives of Biological Interest. XIX: Case of Nitrate Derivatives of Tetrahydro-4,5,6,7 Benzofurans and Benzo (6) Thiophenes" Europ. J. Medicin. Chem.; FRA; DA. 1979; vol. 14; No. 6; pp. 549-552.

*Primary Examiner* — Audrea B Coniglio
(74) *Attorney, Agent, or Firm* — Goodwin Procter LLP

(57) ABSTRACT

Described herein are compounds that act as antimicrobial agents, compositions comprising these compounds, and methods of their use in to treating infections caused by *Helicobacter pylori* (*H. pylori*) or killing or inhibiting the growth of *H. pylori*.

12 Claims, 8 Drawing Sheets

ANTIMICROBIAL AGENTS AND COMPOSITIONS AND USES THEREOF

CROSS-REFERENCE TO RELATED APPLICATIONS

This application is a continuation of International Application Number PCT/US2020/51114 filed Sep. 16, 2020, which claims priority to U.S. Ser. No. 62/901,126, filed Sep. 16, 2019, and U.S. Ser. No. 62/901,127 filed Sep. 16, 2019, the contents of each of which are incorporated herein by reference.

BACKGROUND

*Helicobacter pylori* (*H. pylori*) is a gram-negative, microaerophilic bacterium that colonizes in the gastric mucosa of its host. *H. pylori* infection is widespread with seroprevalence in the developed world between 30-60%. Infection with the bacterium is usually contracted during childhood and patients remain infected for life unless treated. *H. pylori* infection has been shown to result in the development of gastritis, peptic ulcer, and mucosa-associated lymphoid tissue (MALT) lymphoma and has been linked to gastric adenocarcinoma. Drug resistance is prevalent in clinical isolates of *H. pylori*. Antibiotics with new targets and mechanisms of action are needed to treat *H. pylori* infections. New antimicrobial agents are needed to treat infections caused by *H. pylori*.

SUMMARY

Provided herein, in part, are compounds that can be used as antimicrobial agents in the inhibition of the growth or killing of *H. pylori* and treatment of infections and disorders associated with *H. pylori*, such as gastrointestinal disorders. In some embodiments, the *H. pylori* comprises a group of strains. In some embodiments, the *H. pylori* is resistant to at least one drug (e.g. multidrug-resistant *H. pylori*).

In one aspect, described herein is a method of killing or inhibiting the growth of *H. pylori*, the method comprising contacting *H. pylori* with an effective amount of a compound of Formula (I)

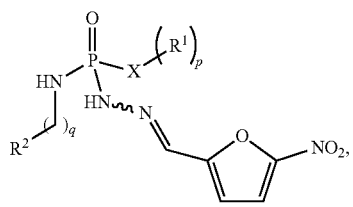

or a pharmaceutically acceptable salt thereof, wherein $R^1$ is hydrogen, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); $R^2$ is hydrogen, substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N=C—$R^{Z1}$, wherein —N=C—$R^{Z1}$ can exist in the E or Z configuration and $R^{Z1}$ is substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, $R^1$ can be taken together with N attached to two instances of $R^1$ to form a 3-6 membered heterocylyl; and q is 0 or 1.

Also described herein is a method of treating an infection caused by *H. pylori* in a subject in need thereof, the method comprising administering to the subject a therapeutically effective amount of a compound of Formula (I)

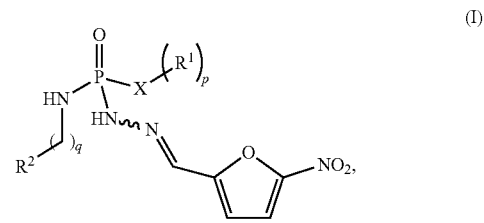

or a pharmaceutically acceptable salt thereof, wherein $R^1$ is hydrogen, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); $R^2$ is hydrogen, substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N=C—$R^{Z1}$, wherein —N=C—$R^{Z1}$ can exist in the E or Z configuration and $R^{Z1}$ is substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, $R^1$ can be taken together with N attached to two instances of $R^1$ to form a 3-6 membered heterocylyl; and q is 0 or 1.

Also described herein is a method of treating a gastrointestinal infection caused by *H. pylori* in a subject in need thereof, the method comprising administering to the subject a a therapeutically effective amount compound of Formula (I)

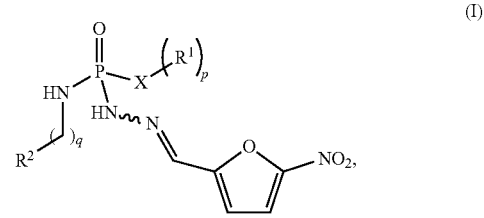

or a pharmaceutically acceptable salt thereof, wherein $R^1$ is hydrogen, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); $R^2$ is hydrogen, substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N=C—$R^{Z1}$, wherein —N=C—$R^{Z1}$ can exist in the E or Z configuration and $R^{Z1}$ is substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, $R^1$ can be taken together with N attached to two instances of $R^1$ to form a 3-6 membered heterocylyl; and q is 0 or 1.

Further described herein is a method of treating a gastrointestinal infection caused by H. pylori in a subject in need thereof, the method comprising administering to the subject a therapeutically effective amount of a compound of Formula (II)

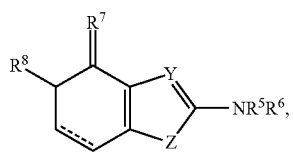

(II)

or pharmaceutically acceptable salt thereof, wherein: ⎯⎯⎯ represents a single or a double bond as valency permits; $R^5$ is hydrogen or oxygen; $R^6$ is selected from the group consisting of hydrogen, oxygen, and substituted or unsubstituted $C_{1-6}$ alkyl, provided that, when $R^5$ is oxygen $R^6$ is oxygen as valency permits; Y is carbon or nitrogen; Z is oxygen or sulfur; $R^7$ is oxygen or nitrogen, wherein the nitrogen is substituted with —NHC(O)NH$_2$, —NHC(O) $C_{1-6}$ alkyl, —C(O)OH, or —C(O)O $C_{1-6}$ alkyl; and $R^8$ is hydrogen, substituted or unsubstituted $C_{1-6}$ alkyl, or —OH, wherein $R^7$ and $R^8$ can be taken together to form a substituted or unsubstituted 5-membered heteroaryl.

Also described herein is a method of treating a gastrointestinal infection caused by H. pylori in a subject in need thereof, the method comprising administering to the subject a therapeutically effective amount of a compound of Formula (III)

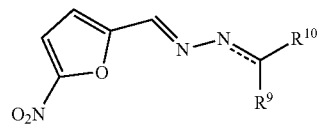

(III)

or pharmaceutically acceptable salt thereof, wherein: ⎯⎯⎯ represents a single or a double bond as valency permits, wherein when ⎯⎯⎯ is a single bond the nitrogen is substituted with hydrogen; $R^9$ is 5-7 membered heteroaryl optionally substituted with —NO$_2$, —NH$_2$, or halogen when ⎯⎯⎯ is a double bond; and when ⎯⎯⎯ is a single bond, $R^9$ is oxo; and $R^{10}$ is hydrogen or $C_{1-6}$ alkenyl optionally substituted with substituted or unsubstituted aryl when ⎯⎯⎯ is a single bond.

Also described herein is a method of treating a gastrointestinal infection caused by H. pylori in a subject in need thereof, the method comprising administering to the subject a therapeutically effective amount of a compound of Formula (IV)

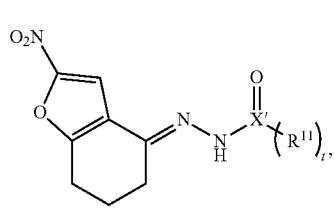

(IV)

or pharmaceutically acceptable salt thereof, wherein: X' is carbon or phosphorus; $R^{11}$ is each and independently selected from the group consisting of substituted or unsubstituted $C_{1-6}$ alkyl, substituted or unsubstituted $C_{1-6}$ alkoxy, —NH$C_{1-6}$ alkyl, —NH$C_6H_5$, and $C_{1-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

Also described herein is a method of killing or inhibiting the growth of H. pylori, the method comprising contacting H. pylori with an effective amount of a compound of Formula (II):

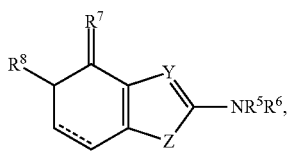

(II)

or pharmaceutically acceptable salt thereof, wherein: ⎯⎯⎯ represents a single or a double bond as valency permits; $R^5$ is hydrogen or oxygen; $R^6$ is selected from the group consisting of hydrogen and substituted or unsubstituted $C_{1-6}$ alkyl, provided that, when $R^5$ is oxygen $R^6$ is oxygen as valency permits; Y is carbon or nitrogen; Z is oxygen or sulfur; $R^7$ is oxygen or nitrogen, wherein the nitrogen is substituted with —NHC(O)NH$_2$, —NHC(O) $C_{1-6}$ alkyl, —C(O)OH, or —C(O)O—$C_{1-6}$ alkyl; and $R^8$ is hydrogen, substituted or unsubstituted $C_{1-6}$ alkyl, or —OH, wherein $R^7$ and $R^8$ can be taken together to form a substituted or unsubstituted 5-membered heteroaryl.

Additionally described herein is a method of killing or inhibiting the growth of H. pylori, the method comprising contacting H. pylori with an effective amount of a compound of Formula (III):

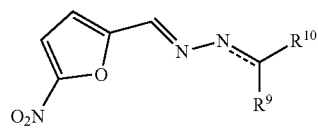

(III)

or pharmaceutically acceptable salt thereof, wherein: ⎯⎯⎯ represents a single or a double bond as valency permits, wherein when ⎯⎯⎯ is a single bond the nitrogen is substituted with hydrogen; $R^9$ is 5-7 membered heteroaryl optionally substituted with —NO$_2$, —NH$_2$, or halogen when ═══ is a double bond; and when ═══ is a single bond, R$^9$ is oxo; and R$^{10}$ is hydrogen or C$_{1-6}$ alkenyl optionally substituted with substituted or unsubstituted aryl when ═══ is a single bond.

Additionally described herein is a method of killing or inhibiting the growth of *H. pylori*, the method comprising contacting *H. pylori* with an effective amount of a compound of Formula (IV):

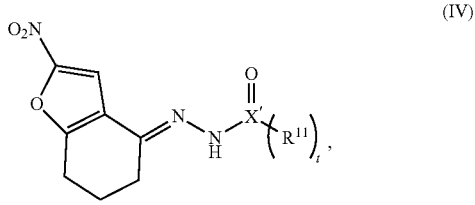

(IV)

or pharmaceutically acceptable salt thereof, wherein: X' is carbon or phosphorus; R$^{11}$ is each and independently selected from the group consisting of substituted or unsubstituted C$_{1-6}$ alkyl, substituted or unsubstituted C$_{1-6}$ alkoxy, —NHC$_{1-6}$ alkyl, —NHC$_6$H$_5$, and C$_{1-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

Additionally provided herein is a method of killing or inhibiting the growth of *H. pylori*, the method comprising contacting *H. pylori* with an effective amount of a compound selected from the group consisting of a compound of Table 1 provided below and pharmaceutically acceptable salts thereof.

Additionally provided herein is a method of treating a gastrointestinal infection caused by *H. pylori* in a subject in need thereof, the method comprising administering to the subject a therapeutically effective amount of a compound selected from the group consisting of a compound of Table 1 provided below and pharmaceutically acceptable salts thereof.

Additionally provided herein is a method of killing or inhibiting the growth of *H. pylori*, comprising contacting *H. pylori* with a composition comprising an effective amount of a compound described herein, e.g., a compound of Formula (I), Formula (II), Formula (III), Formula (IV), or Table 1, or pharmaceutically acceptable salt thereof.

Additionally provided herein is a method of treating a gastrointestinal infection caused by *H. pylori* in a subject in need thereof, the method comprising administering to the subject a pharmaceutical composition comprising a therapeutically effective amount of a compound selected from the group consisting of a compound described herein, e.g., a compound of Formula (I), Formula (II), Formula (III), Formula (IV), or Table 1, or pharmaceutically acceptable salt thereof, and a pharmaceutically acceptable carrier.

DETAILED DESCRIPTION

Figure 1:
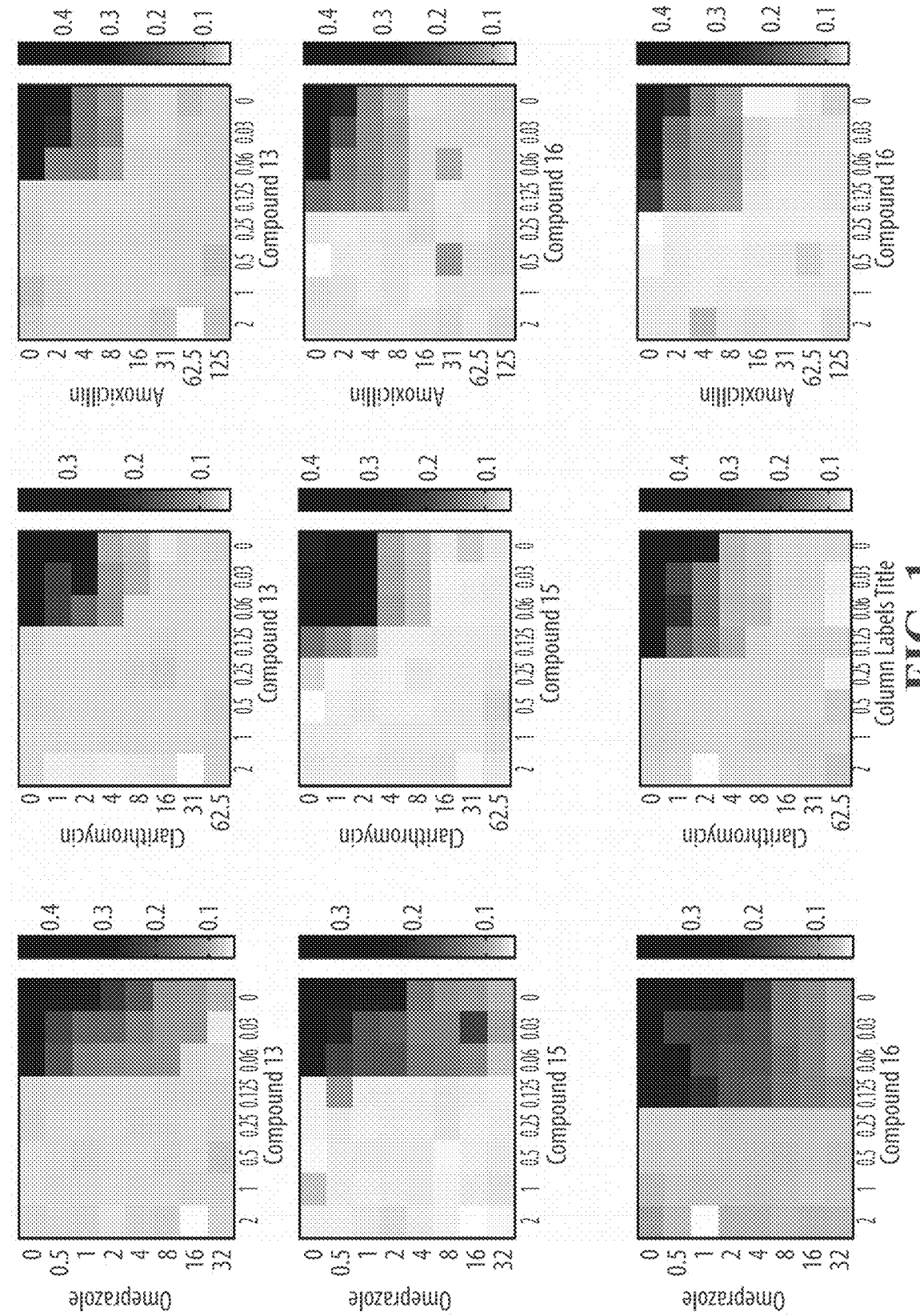
FIG. 1 shows a synergistic effect of Compound 1, Compounds 13, 15, and 16 tested with amoxicillin, clarithromysin, omeprazole, and pantoprazole.

The compounds and compositions described herein can be antimicrobial agents that kill and/or inhibit the growth of strains of *H. pylori*, including *H. pylori* resistant to at least one known drug. In some embodiments, the compounds or compositions can be used the treat a gastrointestinal infection in a subject caused by strains of *H. pylori*.

Compounds

One feature of the present disclosure relates to compounds that act as antimicrobial agents against *H. pylori*. For example, disclosed is a compound of Formula (I):

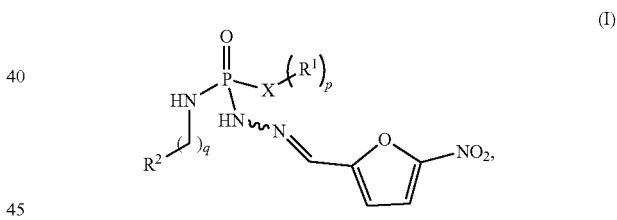

(I)

or a pharmaceutically acceptable salt thereof, wherein R$^1$ is hydrogen, substituted or unsubstituted C$_{1-6}$ alkyl (e.g., —CH$_3$, —CH$_2$CH$_3$, C$_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); R$^2$ is hydrogen, substituted or unsubstituted C$_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N═C—R$^{Z1}$, wherein —N═C—R$^{Z1}$ can exist in the E or Z configuration and R$^{Z1}$ is substituted or unsubstituted C$_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, R$^1$ can be taken together with N attached to two instances of R$^1$ to form a 3-6 membered heterocyclyl; and q is 0 or 1.

In some embodiments, $R^1$ is unsubstituted or substituted $C_{1-6}$ alkyl (e.g., —$CH_3$, —$CH_2CH_3$, $C_{1-6}$ haloalkyl, aralkyl, e.g., benzyl) or substituted or unsubstituted cycloalkyl (e.g., 3 to 8-membered cycloalkyl) and $R^2$ is substituted or unsubstituted aryl or substituted or unsubstituted heteroaryl. In some embodiments, $R^1$ is unsubstituted $C_{1-6}$ alkyl (e.g., —$CH_3$ or —$CH_2CH_3$) and $R^2$ is substituted or unsubstituted aryl or substituted or unsubstituted heteroaryl. In some embodiments, $R^3$ is —N=C—$R^{Z1}$ existing in the E or Z configuration.

In some embodiments, the compound of Formula (I) is a compound of Formula (I-a)

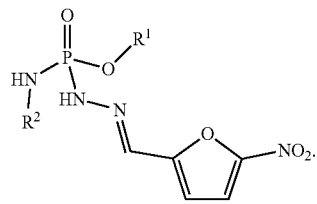

(I-a)

In some embodiments, the compound of Formula (I) is a compound of Formula (I-b)

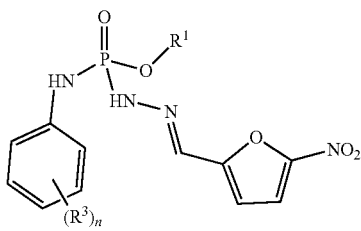

(I-b)

wherein $R^3$ is halo (e.g., —F, —Cl), nitro, cyano, —$CO_2R^4$, —$C(O)R^4$, —$N(R^4)(R^5)$, —$C(O)N(R^4)(R^5)$, —$N(R^4)C(O)R^5$, —$OC(O)N(R^4)$, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), or —$OR^4$; each of $R^4$ and $R^5$ is independently hydrogen, substituted or unsubstituted $C_{1-6}$ alkyl (e.g., —$CH_3$), substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); and n is 0, 1, 2, 3, 4, or 5, wherein if n is 0, then the phenyl is an unsubstituted phenyl.

In some embodiments, $R^1$ is substituted $C_{1-6}$ alkyl (e.g., $C_{1-6}$ haloalkyl or substituted or substituted aralkyl, e.g., substituted or unsubstituted benzyl). In some embodiments, $R^1$ is unsubstituted $C_{1-6}$ alkyl (e.g., —$CH_3$ or —$CH_2CH_3$). In some embodiments, $R^3$ is halo (e.g., —F or —Cl), substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), or substituted or unsubstituted $C_{1-6}$ alkoxy (e.g., —$OCH_3$ or $C_{1-6}$ haloalkoxy, e.g., —$OCF_3$).

In some embodiments, the compound of Formula (I) is a compound of Formula (I-c)

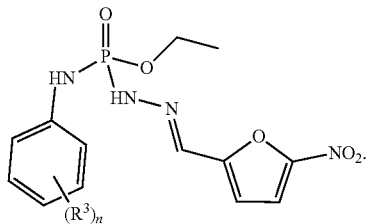

(I-c)

In some embodiments, $R^3$ is —$CH_3$ and n is 1. In some embodiments, $R^3$ is —$OCH_3$ and n is 1. In some embodiments, $R^3$ is —Cl and n is 1 or 2. In some embodiments, $R^3$ is —Cl and n is 1. In some embodiments, $R^3$ is —Cl and n is 2. In some embodiments, $R^3$ is not halo. In some embodiments, n is 0.

Also featured herein is a compound of Formula (II):

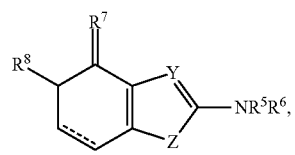

(II)

wherein $≡≡≡$ represents a single or a double bond as valency permits; $R^5$ is hydrogen or oxygen; $R^6$ is selected from the group consisting of hydrogen, oxygen, and substituted or unsubstituted $C_{1-6}$ alkyl, provided that, when $R^5$ is oxygen $R^6$ is oxygen as valency permits; Y is carbon or nitrogen; Z is oxygen or sulfur; $R^7$ is oxygen or nitrogen, wherein the nitrogen is substituted with —$NHC(O)NH_2$, —$NHC(O)$ $C_{1-6}$ alkyl, —$C(O)OH$, or —$C(O)O$ $C_{1-6}$ alkyl; and $R^8$ is hydrogen, substituted or unsubstituted $C_{1-6}$ alkyl, or —OH, wherein $R^7$ and $R^8$ can be taken together to form a substituted or unsubstituted 5-membered heteroaryl.

In some embodiments, Y is nitrogen and Z is sulfur. In some embodiments, $R^7$ and $R^8$ can be taken together to form a substituted or unsubstituted 5-membered heteroaryl, e.g., furanyl.

Also featured herein is a compound of Formula (III):

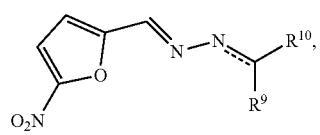

(III)

wherein $≡≡≡$ represents a single or a double bond as valency permits, wherein when $≡≡≡$ is a single bond the nitrogen is substituted with hydrogen; $R^9$ is 5-7 membered heteroaryl optionally substituted with —$NO_2$, —$NH_2$, or halogen when $≡≡≡$ is a double bond; and when $≡≡≡$ is a single bond, $R^9$ is oxo; and $R^{10}$ is hydrogen or $C_{1-6}$ alkenyl optionally substituted with substituted or unsubstituted aryl when $≡≡≡$ is a single bond.

In some embodiments, $R^9$ is furanyl optionally substituted with —$NO_2$, —$NH_2$, —$CO_2H$, or halogen when $≡≡≡$ is a double bond. In some embodiments, $R^9$ is furanyl optionally substituted with —$NO_2$.

Also featured herein is a compound of Formula (IV):

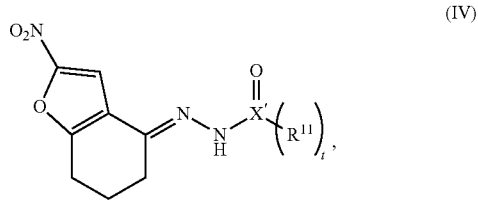

wherein X' is carbon or phosphorus; R¹¹ is each and independently selected from the group consisting of substituted or unsubstituted $C_{1-6}$ alkyl, substituted or unsubstituted $C_{1-6}$ alkoxy, —$NHC_{1-6}$ alkyl, —$NHC_6H_5$, and $C_{1-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

In some embodiments, X' is phosphorus. In some embodiments, R¹¹ is each and independently selected from the group consisting of substituted or unsubstituted $C_{1-6}$ alkoxy, and —$NHC_6H_5$. In some embodiments, R¹¹ is each and independently selected from the group consisting of substituted or unsubstituted ethoxy (e.g., unsubstituted ethoxy), and —$NHC_6H_5$.

In an embodiment, the compound is a compound shown in Table 1.

TABLE 1

Exemplary compounds.

| Compound Number | Compound |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |

TABLE 1-continued
Exemplary compounds.
| Compound Number | Compound |
|---|---|
| 10 | 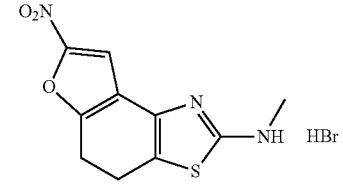 |
| 11 | 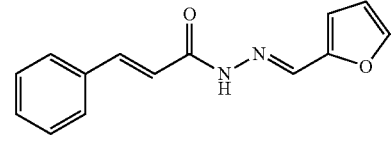 |
| 12 | 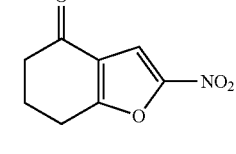 |
| 13 | 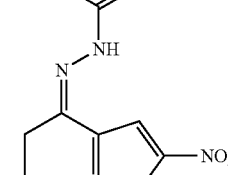 |
| 14 | 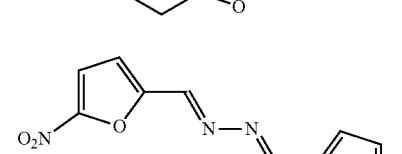 |
| 15 | 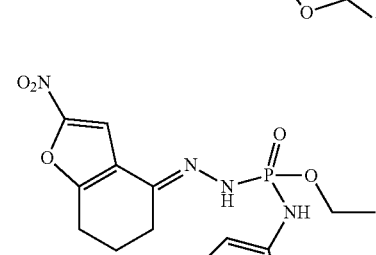 |
| 16 | 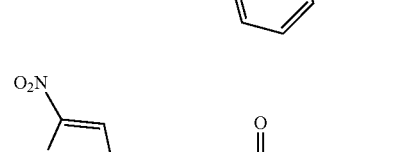 |
| 17 | |
| 18 | |
| 19 | |
| 20 | |

TABLE 1-continued

Exemplary compounds.

| Compound Number | Compound |
|---|---|
| 21 | 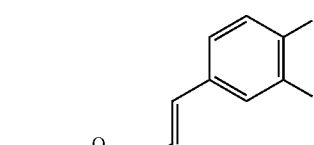 |

Methods of Use

Compounds and compositions described herein (e.g., a compound of Formula (I), Formula (II), Formula (III), or Formula (IV), Table 1, or a pharmaceutically acceptable salt thereof or a composition comprising a compound of Formula (I), Formula (II), Formula (III), Formula (IV), Table 1, or a pharmaceutically acceptable salt thereof) can be used to kill and/or inhibit the growth of a gram-negative bacterium such as *H. pylori*. In some embodiments, *H. pylori* comprises a group of strains. In some embodiments, the strain of *H. pylori* is selected from 49503, 43504, and 51932. In some embodiments, *H. pylori* is resistant to at least one known drug.

The methods can be used to treat or prevent a infection in a subject in need thereof. Compounds and compositions described herein (e.g., a compound of Formula (I), Formula (II), Formula (III), or Formula (IV), Table 1, or a pharmaceutically acceptable salt thereof or a composition comprising a compound of Formula (I), Formula (II), Formula (III), Formula (IV), Table 1, or a pharmaceutically acceptable salt thereof) can be used to treat an infection caused by a gram-negative bacterium such as *H. pylori*. In some embodiments, *H. pylori* comprises a group of strains. In some embodiments, the strain of *H. pylori* is selected from 49503, 43504, and 51932. In some embodiments, *H. pylori* is resistant to at least one known drug. In some embodiments, the infection is a nosocomial infection. In some embodiments, the infection is a community-acquired infection.

In some embodiments, the infection is a gastrointestinal infection. In some embodiments, the gastrointestinal infection is caused by a gram-negative bacterium. In some embodiments, the gastrointestinal gram-negative bacterium that causes the gastrointestinal infection is *H. pylori*. In some embodiments, the *H. pylori* that causes the gastrointestinal infection is resistant to at least one known drug. In some embodiments, the gastrointestinal infection is caused by a bacterium.

In some embodiments, the gastrointestinal infection is a nosocomial infection. In some embodiments, the gastrointestinal infection is a community-acquired infection.

In some embodiments, the gastrointestinal infection can be treated or prevented by administering to the subject a compound or composition described herein.

In some embodiments, the gastrointestinal infection is a stomach infection. In some embodiments, the gastrointestinal infection is a peptic ulcer. In some embodiments, the gastrointestinal infection is a gastric ulcer. In some embodiments, the gastrointestinal infection is a duodenal ulcer. In some embodiments, the gastrointestinal infection is gastritis. In some embodiments, the gastrointestinal infection is chronic gastritis. In some embodiments, the gastrointestinal infection is gastric mucosal inflammation.

The compounds described herein can be administered to cells in culture, e.g. in vitro or ex vivo, or to a subject, e.g., in vivo, or applied to an object to treat or prevent a variety of bacterial infection, including those described herein below. In some embodiments, the compounds and/or compositions inhibit the growth of bacteria and/or decrease bacterial load in a subject or on an object.

In some embodiments, the compounds described herein or a pharmaceutically acceptable salt thereof is administered to the subject in combination with at least one additional agent. In some embodiments, the additional agent is an antibiotic. In some embodiments, the additional agent is an antibiotic selected from the group consisting of an amoxicillin, tetracyline, metronidazole, or clarithromycin. In some embodiments, the additional agent is an amoxicillin. In some embodiments, the additional agent is a clarithromycin. In some embodiments, the additional agent is an acid suppressor. In some embodiments, the additional agent is an acid suppressor selected from the group consisting of omeprazole, pantoprazole, ranitidine bismuth citrate, and bismuth subsalicylate. In some embodiments, the additional agent is an acid suppressor is omeprazole. In some embodiments, the additional agnet is an acid suppressor is pantoprazole.

In some embodiments, the method used to treat or prevent a gastrointestinal infection in a subject further comprises contacting *H. pylori*, with at least one other anti-microbial agent. In some embodiments, the anti-microbial agent is an anti-microbial peptide. In some embodiments, the anti-microbial peptide is β-defensin. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof. In some embodiments, the additional agent is an aminoglycoside antibiotic. In some embodiments, the additional agent is gentamicin. In some embodiments, the additional agent is cationic antimicrobial peptide (CAMP).

In some embodiments, the compounds described herein or a pharmaceutically acceptable salt thereof and the additional agent are administered consecutively. In some embodiments, the compound described herein or a pharmaceutically acceptable salt thereof and the additional agent are administered simultaneously.

Additional methods of use provided by the present disclosure include the following:

In one aspect, described herein is a method of killing or inhibiting the growth of *H. pylori*, the method comprising contacting *H. pylori* with an effective amount of a compound of Formula (I)

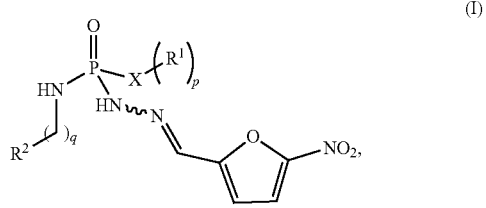

or a pharmaceutically acceptable salt thereof, wherein $R^1$ is hydrogen, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); $R^2$ is hydrogen, substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N=C—$R^{Z1}$, wherein —N=C—$R^{Z1}$ can exist in the E or Z configuration and $R^{Z1}$ is substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, $R^1$ can be taken together with N attached to two instances of $R^1$ to form a 3-6 membered heterocylyl; and q is 0 or 1.

In some embodiments, the *H. pylori* is a group of strains. In some embodiments, the strain is selected from the group consisting of 49503, 43504, and 51932. In some embodiments, the strain is 49503. In some embodiments, the strain is 43504. In some embodiments, the strain is 51932. In some embodiments, the killing or inhibiting the growth of *H. pylori* is in vivo, of in a body of a subject. In some embodiments, the compound of Formula (I) or a pharmaceutically acceptable salt thereof is administered to the subject in combination with at least one additional agent. In some embodiments, the additional agent is an antibiotic. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, amoxicillin, tetracycline, metronidazole, clarithromycin and combinations of two or more thereof. In some embodiments, the additional agent is an antibiotic is amoxicillin. In some embodiments, the additional agent is an antibiotic is clarithromycin. In some embodiments, the additional agent is an acid suppressor. In some embodiments, the additional agent is an acid suppressor selected from the group consisting of omeprazole, pantoprazole, ranitidine bismuth citrate, and bismuth subsalicylate. In some embodiments, the additional agent is an acid suppressor is omeprazole. In some embodiments, the additional agent is an acid suppressor is pantoprazole. In some embodiments, the additional agent is an anti-microbial agent. In some embodiments, the anti-microbial agent is niclosamide. In some embodiments, the compound of Formula (I) or a pharmaceutically acceptable salt thereof and the additional agent are administered consecutively. In some embodiments, the compound of Formula (I) or a pharmaceutically acceptable salt thereof and the additional agent are administered simultaneously.

In some embodiments, $R^1$ is unsubstituted or substituted $C_{1-6}$ alkyl (e.g., —$CH_3$, —$CH_2CH_3$, $C_{1-6}$ haloalkyl, aralkyl, e.g., benzyl) or substituted or unsubstituted cycloalkyl (e.g., 3 to 8-membered cycloalkyl) and $R^2$ is substituted or unsubstituted aryl or substituted or unsubstituted heteroaryl. In some embodiments, $R^1$ is unsubstituted $C_{1-6}$ alkyl (e.g., —$CH_3$ or —$CH_2CH_3$) and $R^2$ is substituted or unsubstituted aryl or substituted or unsubstituted heteroaryl. In some embodiments, $R^2$ is —N=C—$R^{Z1}$ existing in the E or Z configuration.

In some embodiments, the compound of Formula (I) is a compound of Formula (I-a)

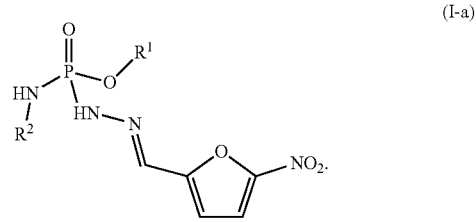

(I-a)

In some embodiments, the compound of Formula (I) is a compound of Formula (I-b)

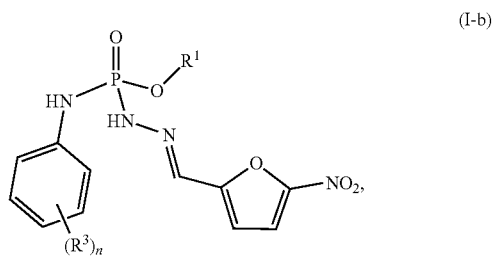

(I-b)

wherein $R^3$ is halo (e.g., —F, —Cl), nitro, cyano, —$CO_2R^4$, —$C(O)R^4$, —$N(R^4)(R^5)$, —$C(O)N(R^4)(R^5)$, —$N(R^4)C(O)R^5$, —$OC(O)N(R^4)$, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), or —$OR^4$; each of $R^4$ and $R^5$ is independently hydrogen, substituted or unsubstituted $C_{1-6}$ alkyl (e.g., —$CH_3$), substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); and n is 0, 1, 2, 3, 4, or 5, wherein if n is 0, then the phenyl is an unsubstituted phenyl. In some embodiments, $R^1$ is substituted $C_{1-6}$ alkyl (e.g., $C_{1-6}$ haloalkyl or substituted or substituted aralkyl, e.g., substituted or unsubstituted benzyl). In some embodiments, $R^1$ is unsubstituted $C_{1-6}$ alkyl (e.g., —$CH_3$ or —$CH_2CH_3$). In some embodiments, $R^3$ is halo (e.g., —F or —Cl), substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), or substituted or unsubstituted $C_{1-6}$ alkoxy (e.g., —$OCH_3$ or $C_{1-6}$ haloalkoxy, e.g., —$OCF_3$).

In some embodiments, the compound of Formula (I) is a compound of Formula (I-c)

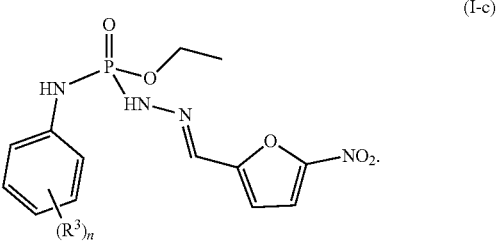

(I-c)

In some embodiments, R³ is —CH₃ and n is 1. In some embodiments, R³ is —OCH₃ and n is 1. In some embodiments, R³ is —Cl and n is 1 or 2. In some embodiments, R³ is —Cl and n is 1. In some embodiments, R³ is —Cl and n is 2. In some embodiments, n is 0.

Also described herein is a method of treating an infection caused by *H. pylori* in a subject in need thereof, the method comprising administering to the subject a therapeutically effective amount of a compound of Formula (I)

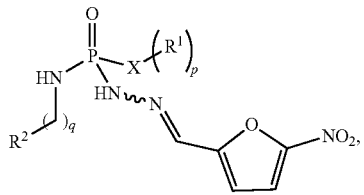

(I)

or a pharmaceutically acceptable salt thereof, wherein R¹ is hydrogen, substituted or unsubstituted C₁₋₆ alkyl (e.g., —CH₃, —CH₂CH₃, C₁₋₆ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); R² is hydrogen, substituted or unsubstituted C₁₋₆ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N═C—R^{Z1}, wherein —N═C—R^{Z1} can exist in the E or Z configuration and R^{Z1} is substituted or unsubstituted C₁₋₆ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, R¹ can be taken together with N attached to two instances of R¹ to form a 3-6 membered heterocylyl; and q is 0 or 1.

In some embodiments, R¹ is unsubstituted or substituted C₁₋₆ alkyl (e.g., —CH₃, —CH₂CH₃, C₁₋₆ haloalkyl, aralkyl, e.g., benzyl) or substituted or unsubstituted cycloalkyl (e.g., 3 to 8-membered cycloalkyl) and R² is substituted or unsubstituted aryl or substituted or unsubstituted heteroaryl. In some embodiments, R¹ is unsubstituted C₁₋₆ alkyl (e.g., —CH₃ or —CH₂CH₃) and R² is substituted or unsubstituted aryl or substituted or unsubstituted heteroaryl. In some embodiments, R² is —N═C—R^{Z1} existing in the E or Z configuration.

In some embodiments, the compound of Formula (I) is a compound of Formula (I-a)

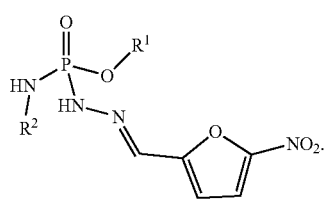

(I-a)

In some embodiments, the compound of Formula (I) is a compound of Formula (I-b)

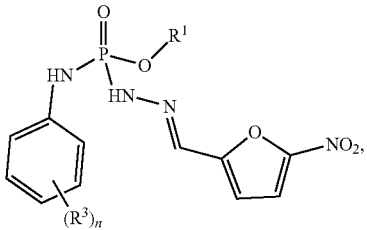

(I-b)

wherein R³ is halo (e.g., —F, —Cl), nitro, cyano, —CO₂R⁴, —C(O)R⁴, —N(R⁴)(R⁵), —C(O)N(R⁴)(R⁵), —N(R⁴)C(O)R⁵, —OC(O)N(R⁴), substituted or unsubstituted C₁₋₆ alkyl (e.g., —CH₃, —CH₂CH₃, C₁₋₆ haloalkyl, substituted or substituted aralkyl, e.g., substituted or unsubstituted benzyl), or —OR⁴; each of R⁴ and R⁵ is independently hydrogen, substituted or unsubstituted C₁₋₆ alkyl (e.g., —CH₃), substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); and n is 0, 1, 2, 3, 4, or 5, wherein if n is 0, then the phenyl is an unsubstituted phenyl. In some embodiments, R¹ is substituted C₁₋₆ alkyl (e.g., C₁₋₆ haloalkyl or substituted or substituted aralkyl, e.g., substituted or unsubstituted benzyl). In some embodiments, R¹ is unsubstituted C₁₋₆ alkyl (e.g., —CH₃ or —CH₂CH₃). In some embodiments, R³ is halo (e.g., —F or —Cl), substituted or unsubstituted C₁₋₆ alkyl (e.g., —CH₃, —CH₂CH₃, C₁₋₆ haloalkyl, substituted or substituted aralkyl, e.g., substituted or unsubstituted benzyl), or substituted or unsubstituted C₁₋₆ alkoxy (e.g., —OCH₃ or C₁₋₆ haloalkoxy, e.g., —OCF₃).

In some embodiments, the compound of Formula (I) is a compound of Formula (I-c)

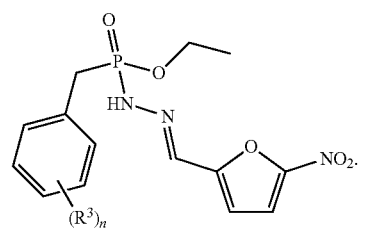

(I-c)

In some embodiments, R³ is —CH₃ and n is 1. In some embodiments, R³ is —OCH₃ and n is 1. In some embodiments, R³ is —Cl and n is 1 or 2. In some embodiments, R³ is —C₁ and n is 1. In some embodiments, R³ is —Cl and n is 2. In some embodiments, n is 0.

In some embodiments, the infection is a bloodstream infection. In some embodiments, the infection is a respiratory infection. In some embodiments, the respiratory infection is pneumonia. In some embodiments, the infection is osteomyelitis. In some embodiments, the infection is endocarditis. In some embodiments, the infection is cellulitis. In some embodiments, the infection is meningitis. In some embodiments, the infection is the result of a wound. In some embodiments, the wound is a surgical wound. In some embodiments, the wound is an ulcer. In some embodiments, the ulcer is a pressure ulcer. In some embodiments, the infection is a urinary tract infection. In some embodiments, the wound is a skin abscess. In some embodiments, the wound is a traumatic wound. In some embodiments, the infection is a community-acquired infection. In some embodiments, the infection is a nosocomial infection. In some embodiments, the composition is administered orally, intranasally, intramuscularly, intravenously, subcutaneously, or transdermally. In some embodiments, the composition is administered to the subject chronically or acutely. In some embodiments, the composition is administered to the subject in a single dose per day. In some embodiments, the composition is administered to the subject in multiple doses per day (e.g., 1, 2, 3, 4, or 5 times per day). In some embodiments, the composition is administered to the subject for 1, 2, 5, or 10 days. In some embodiments, the compound of Formula (I) or a pharmaceutically acceptable salt thereof is administered to the subject in combination with at least one additional therapeutic agent. In some embodiments, the additional therapeutic agent is an antibiotic. In some embodiments, the additional therapeutic agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof. In some embodiments, the additional therapeutic agent is an aminoglycoside antibiotic. In some embodiments, the additional therapeutic agent is gentamicin. In some embodiments, the additional therapeutic agent is cationic antimicrobial peptide (CAMP). In some embodiments, the cationic antimicrobial peptide is defensin 1. In some embodiments, the compound of Formula (I) or a pharmaceutically acceptable salt thereof and the additional therapeutic agent are administered consecutively. In some embodiments, the compound of Formula (I) or a pharmaceutically acceptable salt thereof and the additional therapeutic agent are administered simultaneously.

Also described herein is a method of treating a gastrointestinal infection caused by *H. pylori* in a subject in need thereof, the method comprising administering to the subject a therapeutically effective amount compound of Formula (I)

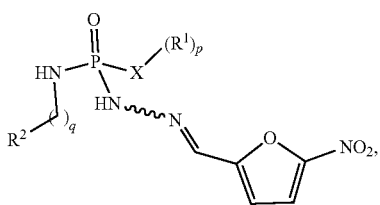

(I)

or a pharmaceutically acceptable salt thereof, wherein $R^1$ is hydrogen, substituted or unsubstituted $C_{1-6}$ alkyl (e.g., —$CH_3$, —$CH_2CH_3$, $C_{1-6}$ haloalkyl, substituted or substituted aralkyl, e.g., substituted or unsubstituted benzyl), substituted or unsubstituted aryl, or substituted or unsubstituted cycloalkyl (e.g., 3 to 8-membered cycloalkyl); $R^2$ is hydrogen, substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl), or —N═C—$R^{Z1}$, wherein —N═C—$R^{Z1}$ can exist in the E or Z configuration and $R^{Z1}$ is substituted or unsubstituted $C_{1-6}$ alkyl, substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); X is nitrogen or oxygen, wherein when X is nitrogen p is 2; and when X is oxygen p is 1; p is 1 or 2, wherein when p is 2, $R^1$ can be taken together with N attached to two instances of $R^1$ to form a 3-6 membered heterocylyl; and q is 0 or 1.

In some embodiments, the *H. pylori* is a group of strains. In some embodiments, the strain is selected from the group consisting of 49503, 43504, and 51932. In some embodiments, the strain is 49503. In some embodiments, the strain is 43504. In some embodiments, the strain is 51932. In some embodiments, the gastrointestinal infection is stomach infection. In some embodiments, the gastrointestinal infection is peptic ulcer. In some embodiments, the gastrointestinal infection is gastric ulcer. In some embodiments, the gastrointestinal infection is duodenal ulcer. In some embodiments, the gastrointestinal infection is gastritis. In some embodiments, the gastrointestinal infection is chronic gastritis. In some embodiments, the gastrointestinal infection is gastric mucosal inflammation. In some embodiments, the composition is administered orally, intranasally, intramuscularly, intravenously, subcutaneously, or transdermally. In some embodiments, the killing or inhibiting the growth of *H. pylori* is in vivo, of in a body of a subject. In some embodiments, the compound of Formula (I) or a pharmaceutically acceptable salt thereof is administered to the subject in combination with at least one additional agent. In some embodiments, the additional agent is an antibiotic. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, amoxicillin, tetracycline, metronidazole, clarithromycin and combinations of two or more thereof. In some embodiments, the additional agent is an antibiotic is amoxicillin. In some embodiments, the additional agent is an antibiotic is clarithromycin. In some embodiments, the additional agent is an acid suppressor. In some embodiments, the additional agent is an acid suppressor is omeprazole. In some embodiments, the additional agent is an acid suppressor is pantoprazole. In some embodiments, the additional agent is an anti-microbial agent. In some embodiments, the anti-microbial agent is niclosamide. In some embodiments, the compound of Formula (I) or a pharmaceutically acceptable salt thereof and the additional agent are administered consecutively. In some embodiments, the compound of Formula (I) or a pharmaceutically acceptable salt thereof and the additional agent are administered simultaneously.

In some embodiments, $R^1$ is unsubstituted or substituted $C_{1-6}$ alkyl (e.g., —$CH_3$, —$CH_2CH_3$, $C_{1-6}$ haloalkyl, aralkyl, e.g., benzyl) or substituted or unsubstituted cycloalkyl (e.g., 3 to 8-membered cycloalkyl) and $R^2$ is substituted or unsubstituted aryl or substituted or unsubstituted heteroaryl. In some embodiments, $R^1$ is unsubstituted or substituted $C_{1-6}$ alkyl (e.g., —$CH_3$ or —$CH_2CH_3$) and $R^2$ is substituted or unsubstituted aryl or substituted or unsubstituted heteroaryl. In some embodiments, $R^2$ is —N═C—$R^{Z1}$ existing in the E or Z configuration.

In some embodiments, the compound of Formula (I) is a compound of Formula (I-a)

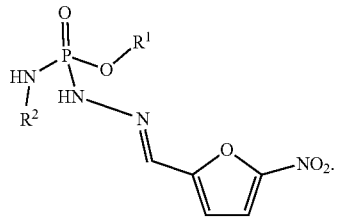

(I-a)

In some embodiments, the compound of Formula (I) is a compound of Formula (I-b)

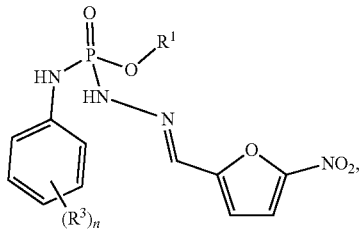

(I-b)

wherein $R^3$ is halo (e.g., —F, —Cl), nitro, cyano, —CO$_2$R$^4$, —C(O)R$^4$, —N(R$^4$)(R$^5$), —C(O)N(R$^4$)(R$^5$), —N(R$^4$)C(O)R$^5$, —OC(O)N(R$^4$), substituted or unsubstituted C$_{1-6}$ alkyl (e.g., —CH$_3$, —CH$_2$CH$_3$, C$_{1-6}$ haloalkyl, substituted or substituted aralkyl, e.g., substituted or unsubstituted benzyl), or —OR$^4$; each of R$^4$ and R$^5$ is independently hydrogen, substituted or unsubstituted C$_{1-6}$ alkyl (e.g., —CH$_3$), substituted or unsubstituted aryl, substituted or unsubstituted heteroaryl, substituted or unsubstituted cycloalkyl (e.g., 3 to 8-membered cycloalkyl), or substituted or unsubstituted heterocyclyl (e.g., 3 to 8-membered heterocyclyl); and n is 0, 1, 2, 3, 4, or 5, wherein if n is 0, then the phenyl is an unsubstituted phenyl.

In some embodiments, R$^1$ is substituted C$_{1-6}$ alkyl (e.g., C$_{1-6}$ haloalkyl or substituted or substituted aralkyl, e.g., substituted or unsubstituted benzyl). In some embodiments, R$^1$ is unsubstituted C$_{1-6}$ alkyl (e.g., —CH$_3$ or —CH$_2$CH$_3$). In some embodiments, R$^3$ is halo (e.g., —F or —Cl), substituted or unsubstituted C$_{1-6}$ alkyl (e.g., —CH$_3$, —CH$_2$CH$_3$, C$_{1-6}$ haloalkyl, substituted or substituted aralkyl, e.g., substituted or unsubstituted benzyl), or substituted or unsubstituted C$_{1-6}$ alkoxy (e.g., —OCH$_3$ or C$_{1-6}$ haloalkoxy, e.g., —OCF$_3$).

In some embodiments, the compound of Formula (I) is a compound of Formula (I-c)

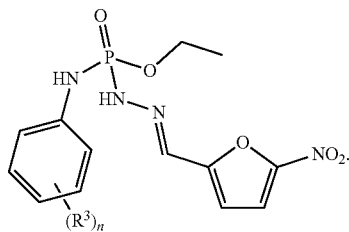

(I-c)

In some embodiments, R$^3$ is —CH$_3$ and n is 1. In some embodiments, R$^3$ is —OCH$_3$ and n is 1. In some embodiments, R$^3$ is —Cl and n is 1 or 2. In some embodiments, R$^3$ is —C$_1$ and n is 1. In some embodiments, R$^3$ is —Cl and n is 2. In some embodiments, n is 0.

Further described herein is a method of treating a gastrointestinal infection caused by *H. pylori* in a subject in need thereof, the method comprising administering to the subject a therapeutically effective amount of a compound of Formula (II)

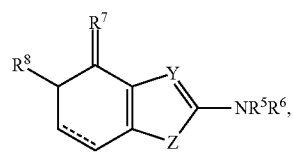

(II)

or pharmaceutically acceptable salt thereof, wherein: ═ ═ ═ represents a single or a double bond as valency permits; R$^5$ is hydrogen or oxygen; R$^6$ is selected from the group consisting of hydrogen, oxygen, and substituted or unsubstituted C$_{1-6}$ alkyl, provided that, when R$^5$ is oxygen R$^6$ is oxygen as valency permits; Y is carbon or nitrogen; Z is oxygen or sulfur; R$^7$ is oxygen or nitrogen, wherein the nitrogen is substituted with —NHC(O)NH$_2$, —NHC(O)C$_{1-6}$ alkyl, —C(O)OH, or —C(O)O C$_{1-6}$ alkyl; and R$^8$ is hydrogen, substituted or unsubstituted C$_{1-6}$ alkyl, or —OH, wherein R$^7$ and R$^8$ can be taken together to form a substituted or unsubstituted 5-membered heteroaryl.

In some embodiments, the *H. pylori* is a group of strains. In some embodiments, the strain is selected from the group consisting of 49503, 43504, and 51932. In some embodiments, the strain is 49503. In some embodiments, the strain is 43504. In some embodiments, the strain is 51932. In some embodiments, the gastrointestinal infection is stomach infection. In some embodiments, the gastrointestinal infection is peptic ulcer. In some embodiments, the gastrointestinal infection is gastric ulcer. In some embodiments, the gastrointestinal infection is duodenal ulcer. In some embodiments, the gastrointestinal infection is gastritis. In some embodiments, the gastrointestinal infection is chronic gastritis. In some embodiments, the gastrointestinal infection is gastric mucosal inflammation. In some embodiments, the composition is administered orally, intranasally, intramuscularly, intravenously, subcutaneously, or transdermally. In some embodiments, the killing or inhibiting the growth of *H. pylori* is in vivo, of in a body of a subject. In some embodiments, the compound of Formula (II) or a pharmaceutically acceptable salt thereof is administered to the subject in combination with at least one additional agent. In some embodiments, the additional agent is an antibiotic. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, amoxicillin, tetracycline, metronidazole, clarithromycin and combinations of two or more thereof. In some embodiments, the additional agent is an antibiotic is amoxicillin. In some embodiments, the additional agent is an antibiotic is clarithromycin. In some embodiments, the additional agent is an acid suppressor. In some embodiments, the additional agent is an acid suppressor is omeprazole. In some embodiments, the additional agent is an acid suppressor is pantoprazole. In some embodiments, the additional agent is an anti-microbial agent. In some embodiments, the anti-microbial agent is niclosamide.

Also described herein is a method of treating a gastrointestinal infection caused by *H. pylori* in a subject in need thereof, the method comprising administering to the subject a therapeutically effective amount of a compound of Formula (III)

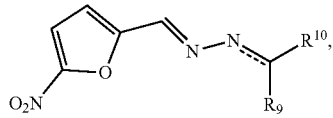

or pharmaceutically acceptable salt thereof, wherein: ═══ represents a single or a double bond as valency permits, wherein when ═══ is a single bond the nitrogen is substituted with hydrogen; $R^9$ is 5-7 membered heteroaryl optionally substituted with —$NO_2$, —$NH_2$, or halogen when ═══ is a double bond; and when ═══ is a single bond, $R^9$ is oxo; and $R^{10}$ is hydrogen or $C_{1-6}$ alkenyl optionally substituted with substituted or unsubstituted aryl when ═══ is a single bond.

In some embodiments, the *H. pylori* is a group of strains. In some embodiments, the strain is selected from the group consisting of 49503, 43504, and 51932. In some embodiments, the strain is 49503. In some embodiments, the strain is 43504. In some embodiments, the strain is 51932. In some embodiments, the gastrointestinal infection is stomach infection. In some embodiments, the gastrointestinal infection is peptic ulcer. In some embodiments, the gastrointestinal infection is gastric ulcer. In some embodiments, the gastrointestinal infection is duodenal ulcer. In some embodiments, the gastrointestinal infection is gastritis. In some embodiments, the gastrointestinal infection is chronic gastritis. In some embodiments, the gastrointestinal infection is gastric mucosal inflammation. In some embodiments, the composition is administered orally, intranasally, intramuscularly, intravenously, subcutaneously, or transdermally. In some embodiments, the killing or inhibiting the growth of *H. pylori* is in vivo, of in a body of a subject. In some embodiments, the compound of Formula (III) or a pharmaceutically acceptable salt thereof is administered to the subject in combination with at least one additional agent. In some embodiments, the additional agent is an antibiotic. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, amoxicillin, tetracycline, metronidazole, clarithromycin and combinations of two or more thereof. In some embodiments, the additional agent is an antibiotic is amoxicillin. In some embodiments, the additional agent is an antibiotic is clarithromycin. In some embodiments, the additional agent is an acid suppressor. In some embodiments, the additional agent is an acid suppressor is omeprazole. In some embodiments, the additional agent is an acid suppressor is pantoprazole. In some embodiments, the additional agent is an anti-microbial agent. In some embodiments, the anti-microbial agent is niclosamide.

Also described herein is a method of treating a gastrointestinal infection caused by *H. pylori* in a subject in need thereof, the method comprising administering to the subject a therapeutically effective amount of a compound of Formula (IV)

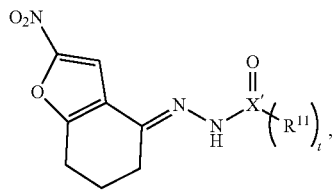

or pharmaceutically acceptable salt thereof, wherein: X' is carbon or phosphorus; $R^{11}$ is each and independently selected from the group consisting of substituted or unsubstituted $C_{1-6}$ alkyl, substituted or unsubstituted $C_{1-6}$ alkoxy, —$NHC_{1-6}$ alkyl, —$NHC_6H_5$, and $C_{1-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

In some embodiments, the *H. pylori* is a group of strains. In some embodiments, the strain is selected from the group consisting of 49503, 43504, and 51932. In some embodiments, the strain is 49503. In some embodiments, the strain is 43504. In some embodiments, the strain is 51932. In some embodiments, the gastrointestinal infection is stomach infection. In some embodiments, the gastrointestinal infection is peptic ulcer. In some embodiments, the gastrointestinal infection is gastric ulcer. In some embodiments, the gastrointestinal infection is duodenal ulcer. In some embodiments, the gastrointestinal infection is gastritis. In some embodiments, the gastrointestinal infection is chronic gastritis. In some embodiments, the gastrointestinal infection is gastric mucosal inflammation. In some embodiments, the composition is administered orally, intranasally, intramuscularly, intravenously, subcutaneously, or transdermally. In some embodiments, the killing or inhibiting the growth of *H. pylori* is in vivo, of in a body of a subject. In some embodiments, the compound of Formula (IV) or a pharmaceutically acceptable salt thereof is administered to the subject in combination with at least one additional agent. In some embodiments, the additional agent is an antibiotic. In some embodiments, the additional agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, amoxicillin, tetracycline, metronidazole, clarithromycin and combinations of two or more thereof. In some embodiments, the antibiotic is amoxicillin. In some embodiments, the antibiotic is clarithromycin. In some embodiments, the additional agent is an acid suppressor. In some embodiments, the additional agent is an acid suppressor is omeprazole. In some embodiments, the additional agent is an acid suppressor is pantoprazole. In some embodiments, the additional agent is an anti-microbial agent. In some embodiments, the anti-microbial agent is niclosamide.

Also described herein is a method of killing or inhibiting the growth of *H. pylori*, the method comprising contacting *H. pylori* with an effective amount of a compound of Formula (II):

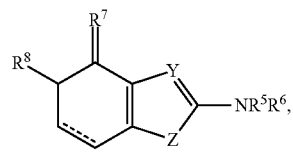

or pharmaceutically acceptable salt thereof, wherein: --- represents a single or a double bond as valency permits; $R^5$ is hydrogen or oxygen; $R^6$ is selected from the group consisting of hydrogen and substituted or unsubstituted $C_{1-6}$ alkyl, provided that, when $R^5$ is oxygen $R^6$ is oxygen as valency permits; Y is carbon or nitrogen; Z is oxygen or sulfur; $R^7$ is oxygen or nitrogen, wherein the nitrogen is substituted with —NHC(O)NH$_2$, —NHC(O)$C_{1-6}$ alkyl, —C(O)OH, or —C(O)O—$C_{1-6}$ alkyl; and $R^8$ is hydrogen, substituted or unsubstituted $C_{1-6}$ alkyl, or —OH, wherein $R^7$ and $R^8$ can be taken together to form a substituted or unsubstituted 5-membered heteroaryl.

In some embodiments, the compound of Formula (II) or a pharmaceutically acceptable salt thereof is administered to the subject in combination with at least one additional therapeutic agent. In some embodiments, the additional therapeutic agent is an antibiotic. In some embodiments, the additional therapeutic agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof. In some embodiments, the additional therapeutic agent is an aminoglycoside antibiotic. In some embodiments, the additional therapeutic agent is gentamicin. In some embodiments, the additional therapeutic agent is cationic antimicrobial peptide (CAMP). In some embodiments, the cationic antimicrobial peptide is defensin 1. In some embodiments, the compound of Formula (II) or a pharmaceutically acceptable salt thereof and the additional therapeutic agent are administered consecutively. In some embodiments, the compound of Formula (II) or a pharmaceutically acceptable salt thereof and the additional therapeutic agent are administered simultaneously.

Additionally described herein is a method of killing or inhibiting the growth of *H. pylori*, the method comprising contacting *H. pylori* with an effective amount of a compound of Formula (III):

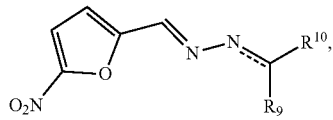

or pharmaceutically acceptable salt thereof, wherein: --- represents a single or a double bond as valency permits, wherein when --- is a single bond the nitrogen is substituted with hydrogen; $R^9$ is 5-7 membered heteroaryl optionally substituted with —NO$_2$, —NH$_2$, or halogen when --- is a double bond; and when --- is a single bond, $R^9$ is oxo; and $R^{1o}$ is hydrogen or $C_{1-6}$ alkenyl optionally substituted with substituted or unsubstituted aryl when --- is a single bond.

In some embodiments, the compound of Formula (III) or a pharmaceutically acceptable salt thereof is administered to the subject in combination with at least one additional therapeutic agent. In some embodiments, the additional therapeutic agent is an antibiotic. In some embodiments, the additional therapeutic agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof. In some embodiments, the additional therapeutic agent is an aminoglycoside antibiotic. In some embodiments, the additional therapeutic agent is gentamicin. In some embodiments, the additional therapeutic agent is cationic antimicrobial peptide (CAMP). In some embodiments, the cationic antimicrobial peptide is defensin 1. In some embodiments, the compound of Formula (III) or a pharmaceutically acceptable salt thereof and the additional therapeutic agent are administered consecutively. In some embodiments, the compound of Formula (III) or a pharmaceutically acceptable salt thereof and the additional therapeutic agent are administered simultaneously.

Additionally described herein is a method of killing or inhibiting the growth of *H. pylori*, the method comprising contacting *H. pylori* with an effective amount of a compound of Formula (IV):

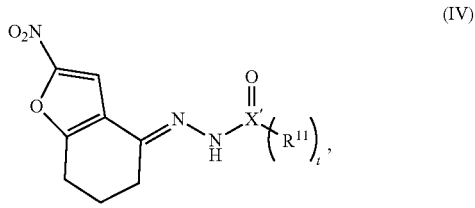

or pharmaceutically acceptable salt thereof, wherein: X' is carbon or phosphorus; $R^{11}$ is each and independently selected from the group consisting of substituted or unsubsistuted $C_{1-6}$ alkyl, substituted or unsubstituted $C_{1-6}$ alkoxy, —NHC$_{1-6}$alkyl, —NHC$_6$H$_5$, and $C_{1-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

In some embodiments, the compound of Formula (IV) or a pharmaceutically acceptable salt thereof is administered to the subject in combination with at least one additional therapeutic agent. In some embodiments, the additional therapeutic agent is an antibiotic. In some embodiments, the additional therapeutic agent is an antibiotic selected from the group consisting of a quinolone, a β-lactam, a cephalosporin, a penicillin, a carbapenem, a lipopetide, an aminoglycoside, a glycopeptide, a macrolide, an ansamycin, a sulfonamide, and combinations of two or more thereof. In some embodiments, the additional therapeutic agent is an aminoglycoside antibiotic. In some embodiments, the additional therapeutic agent is gentamicin. In some embodiments, the additional therapeutic agent is cationic antimicrobial peptide (CAMP). In some embodiments, the cationic antimicrobial peptide is defensin 1. In some embodiments, the compound of Formula (IV) or a pharmaceutically acceptable salt thereof and the additional therapeutic agent are administered consecutively. In some embodiments, the compound of Formula (IV) or a pharmaceutically acceptable salt thereof and the additional therapeutic agent are administered simultaneously.

Additionally provided herein is a method of killing or inhibiting the growth of *H. pylori*, the method comprising contacting *H. pylori* with an effective amount of a compound selected from the group consisting of:

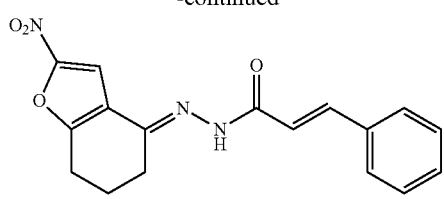
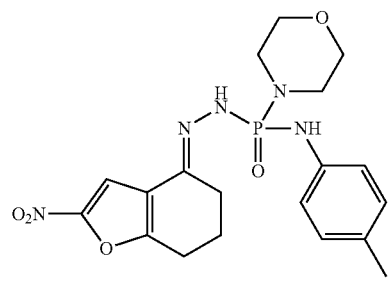
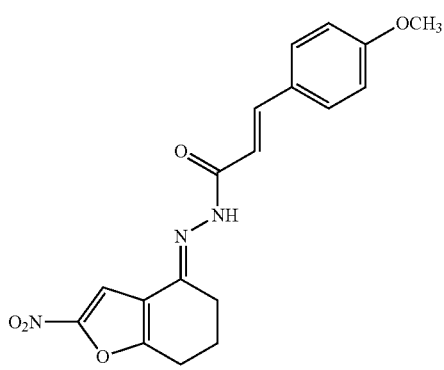
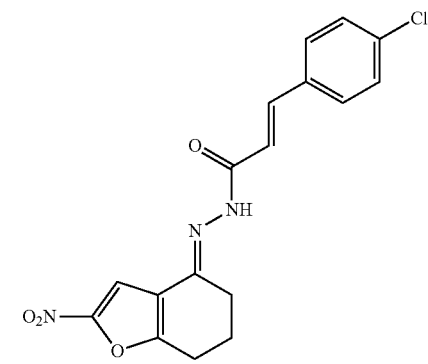
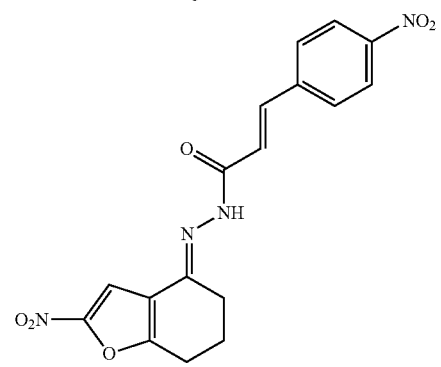
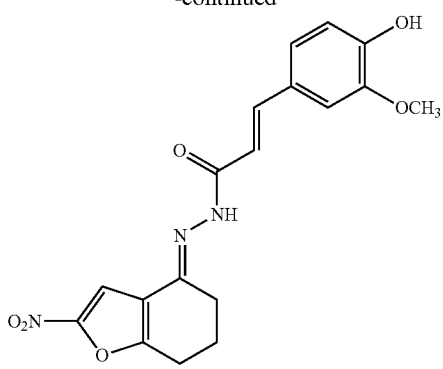
and pharmaceutically acceptable salts thereof.
Additionally provided herein is a method of treating a gastrointestinal infection caused by *H. pylori* in a subject in need thereof, the method comprising administering to the subject a therapeutically effective amount of a compound selected from the group consisting of:
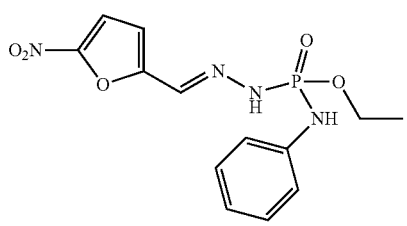
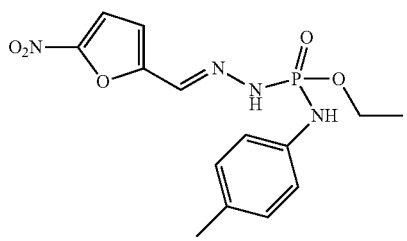
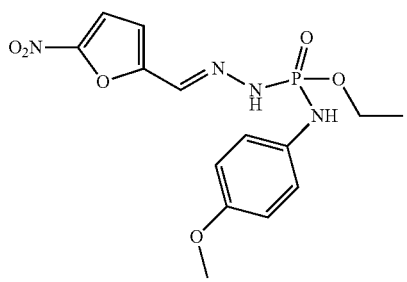
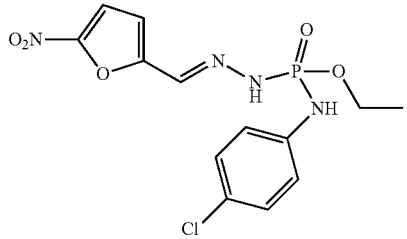

31
-continued
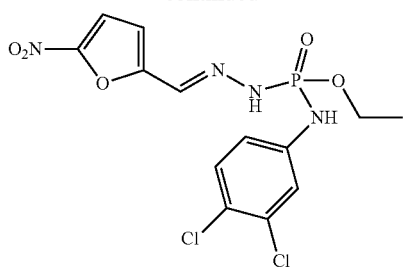
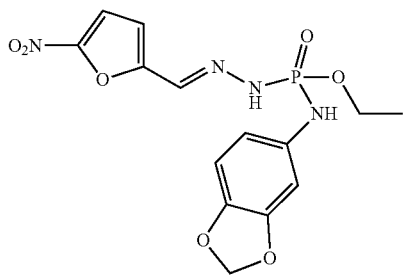
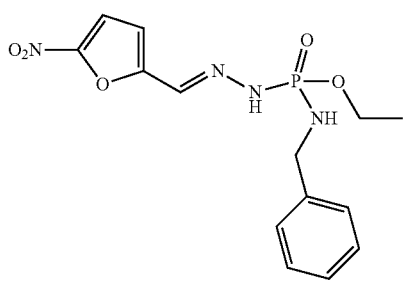 [SMILES: CCOP(=O)(NCc1ccccc1)N/N=C/c1ccc([N+](=O)[O-])o1]
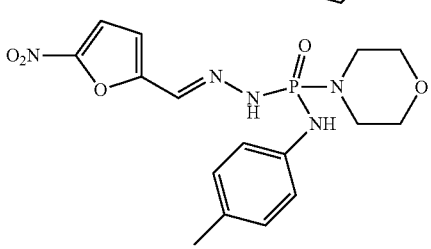
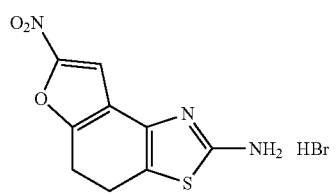 [SMILES: Nc1nc2c(s1)CCc1oc([N+](=O)[O-])cc1-2 ; Br]
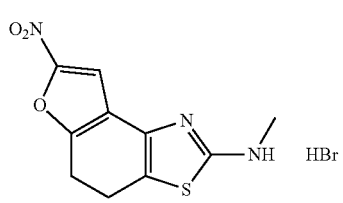
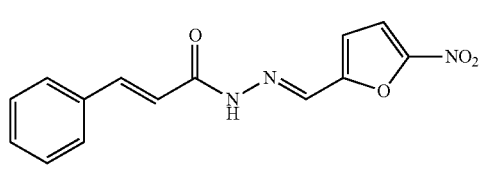 [SMILES: O=C(/C=C/c1ccccc1)N/N=C/c1ccc([N+](=O)[O-])o1]
32
-continued
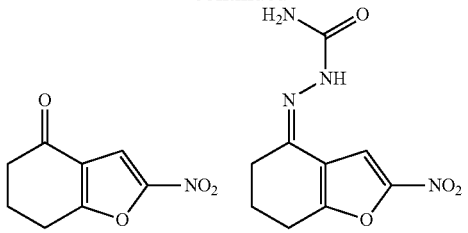
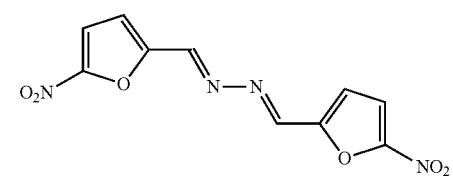
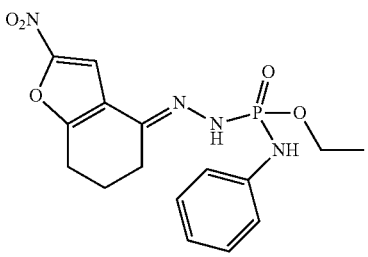
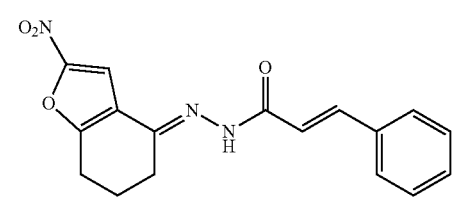 [SMILES: O=C(/C=C/c1ccccc1)N/N=C1\CCCc2oc([N+](=O)[O-])cc21]
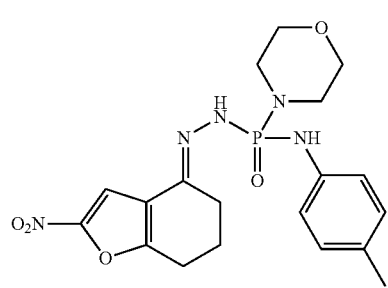 [SMILES: Cc1ccc(NP(=O)(N/N=C2\CCCc3oc([N+](=O)[O-])cc32)N2CCOCC2)cc1]
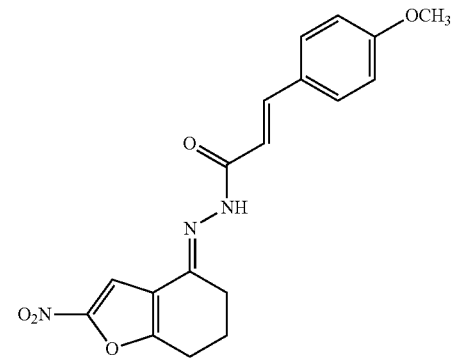 [SMILES: COc1ccc(/C=C/C(=O)N/N=C2\CCCc3oc([N+](=O)[O-])cc32)cc1]

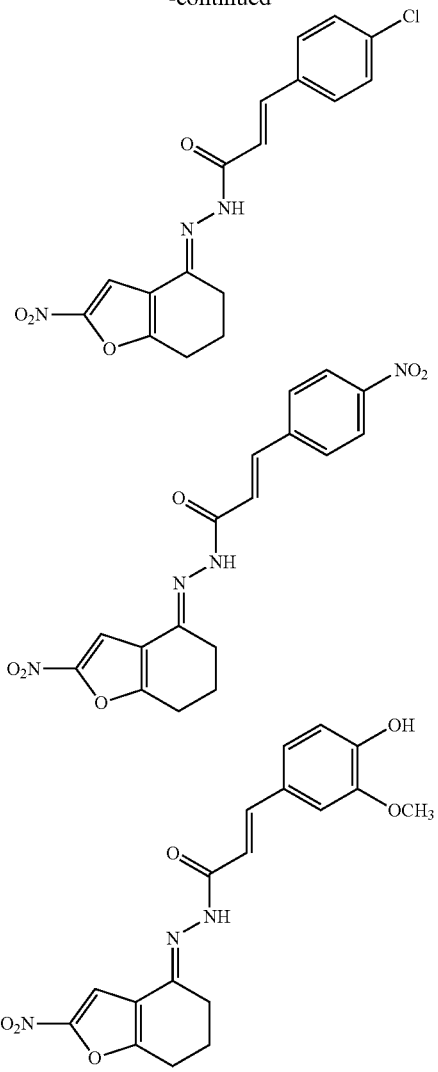

and pharmaceutically acceptable salts thereof.

Additionally provided herein is a method of killing or inhibiting the growth of *H. pylori*, comprising contacting *H. pylori* with a composition comprising an effective amount of a compound described herein, e.g., a compound of Formula (I), Formula (II), Formula (III), Formula (IV), or Table 1, or pharmaceutically acceptable salt thereof.

Additionally provided herein is a method of treating a gastrointestinal infection caused by *H. pylori* in a subject in need thereof, the method comprising administering to the subject a pharmaceutical composition comprising a therapeutically effective amount of a compound selected from the group consisting of a compound described herein, e.g., a compound of Formula (I), Formula (II), Formula (III), Formula (IV), or Table 1, or pharmaceutically acceptable salt thereof, and a pharmaceutically acceptable carrier.

Multiple Drug Resistance

Compositions and methods useful for treating and/or inhibiting acquisition of a multiple drug resistance (MDR) bacteria are described herein. The composition and methods described herein can be used to treat a subject at risk for exposure to or infection with an MDR bacterium. In some embodiments, the MDR bacterium is MDR *H. pylori*. In some embodiments, the MDR bacterium is *H. pylori*. Exemplary compositions and methods generally include use of a compound described herein (e.g., a compound of Formula (I) or a pharmaceutically acceptable salt thereof), including administering to a subject a compound described herein (e.g., a compound of Formula (I) or a pharmaceutically acceptable salt thereof) or a composition comprising a compound described herein (e.g., a compound of Formula (I) or a pharmaceutically acceptable salt thereof) to a subject having a multiple drug resistance (MDR) bacteria or at risk of having a multiple drug resistance (MDR) bacteria. Susceptibility and resistance to anti-bacterials are expressed as either a concentration or a zone diamter for growth inhibition. Clinical anti-bacterial "breakpoints" refer to the minimum inhibitory concentration (MIC) for a given anti-bacterial where there is a high likelihood of treatment failure, and are derived from human clinical studies or from knowledge derived from phamacodynamic and pharmacokinetic techniques applied to animal models. A large number of national societies and organizations set these break-points using various standards, and include the Clinical and Laboratory Standards Institute (CLSI) and the Food and Drug Administration (FDA) in the US, the Swedeish Reference Group for Antibiotics (SRGA), the Japanese Society for Chemotherapy (JSC) etc. [see John Turnidge and David Paterson, Clinical Microbiology Reviews Vol 20 (3), July 2007 pp. 391-408].

Bacteria can employ several mechanisms in attaining MDR, e.g., modification of specific targeted enzyme so it is no longer inactivated by the drug, enzymatic deactivation of antibiotics, decreased cell wall permeability to antibiotic, altered target sites of antibiotic, efflux mechanisms to remove antibiotics, etc. Increased mutation rate as a stress response is a common mechanism for variants in altered sites aned enzymes to arise. Nearly all bacteria, e.g., Staphylococci, Enterococci, Gonococci, Streptococci, *Salmonella, Mycobacterium tuberculosis, Acinetobacter* are able to exhibit MDR. Most bacteria, excluding Mycobacteria, have multiple routes for acquiring and disseminating resistance to a drug. Resistance is spread clonally as bacteria grow. Plasmids can be transferred by conjugation to other bacteria, such as within the Enterobacteriaecae (*E. Coli, Enterobacter* and *Citrobacter* species). Transposition of the resistance gene to other plasmids also increases the ability of the resistant gene to be transferred between different bacteria.

A variety of other pathogens have emerged as multi drug resistant. *Klebsiella pneumoniae* can cause nosocomial wound infections and is resistant to ampicillin. Many strains have acquired resistance to carbenicillin, quinolones, and increasingly to ceftazidime. The bacteria remain largely susceptible to aminoglycosides and cephalosporins. Cutaneous infection from *Leishmania major* generally results in chronic, painless skin lesions. *Leishmania tropica* and *Leishmania infantum-donovani* may be associated with visceralization and more chronic, reactivating illness. While treatment controls the clinical disease, it does not destroy the organism.

Mechanisms of Resistance

Four common mechanisms by which microorganisms exhibit resistance to antimicrobials are:
1. Drug inactivation or modification: e.g. enzymatic deactivation of beta-lactams in some Penicillin-resistant bacteria occurs through the production of β-lactamases which destroy the active part of the lactam. Vancoymycin resistance is typically the enzymatic removal of the last two peptides of the chain reducting its activity ~1000 times.

2. Alteration of drug target site: The bacterium produces a modified protein or enzyme that binds to the drug, rendering it ineffective. For example, penicillin-binding proteins (PBP's) bind to beta-lactam antibiotics blocking their inhibition of cell wall construction. The drug can no longer act at the intended site.
3. Alteration of metabolic pathway: The bacteria utilize alternative pathways that bypass the metabolic pathway that the drug affects. For example, sulfanamides inhibit the synthesis of folic acid early in the bacterial metabolic pathway. Some sulfonamide-resistant bacteria, like mammalian cells, turn to utilizing preformed folic acid from a different pathway that is not affected by the sulfanamide.
4. Efflux pumps: Bacteria reduce drug accumulation by increasing active efflux (pumping out) of the drugs across the cell surface. The resistant bacteria can also reduce drug accumulation by decreasing drug permeability into the cell and/or its interaction once inside. (Efflux pumps are common mechanisms for ciprofloxacin and silver)

In some embodiments, a compound described herein (e.g., a compound of Formula (I) or a pharmaceutically acceptable salt thereof) or composition thereof can prevent or overcome one or more of these mechanisms described above (e.g., when administered to a subject having a bacterial infection or contacting a bacteria).

Mechanisms of Antibacterial Agents

Compositions and methods using a compound described herein (e.g., a compound of Formula (I) or a pharmaceutically acceptable salt thereof) can be used to treat bacterial infection and/or inhibit the growth of bacteria.

Antibacterial action generally falls within one of four mechanisms, three of which involve the inhibition or regulation of enzymes involved in cell wall biosynthesis, nucleic acid metabolism and repair, or protein synthesis. The fourth mechanism involves the disruption of membrane structure, like a pore-former. A common example of a pore-former is polymixin B.

Many of these cellular functions targeted by antibiotics are most active in multiplying cells. Such cells are often rapidly dividing as are cancer cells and some antibacterials have also been found to be useful as anticancer agents.

Some antibacterials inhibit an enzyme necessary for bacterial survival or replication or block an enzymes binding site without contacting the enzyme specifically. These typically are found to interfere with cell wall synthesis, interfere with DNA synthesis, or interfere with protein synthesis. The latter mechanisms are disruption of a cell membrane, causing leakage, disruption of osmotic gradients, and loss of critical cellular contents.

Combination Therapies

In some embodiments, a composition of the present application further comprises one or more additional agents. The additional agent may be selected from any compound or agent known to have or that demonstrates advantageous properties when administered with a compound described herein, e.g., a compound of Formula (I), Formula (II), Formula (III), or Formula (IV) or a pharmaceutically acceptable salt thereof. In some embodiments, a method of treating a subject in need thereof as disclosed herein comprises administering to the subject one or more additional agents. In some embodiments, a compound described herein, e.g., a compound of Formula (I), Formula (II), Formula (III), or Formula (IV) or a pharmaceutically acceptable salt thereof, can be used in combination with an antibiotic. In some embodiments, a compound described herein, e.g., a compound of Formula (I), Formula (II), Formula (III), or Formula (IV) or a pharmaceutically acceptable salt thereof, can be used in combination with an acid suppressor.

In some embodiments, the acid suppressor is selected from omeprazole, pantoprazole, lansoprazole, dexlasoprazole, rabeprazole, rantidine bismuth citrate, bismuth subsalicylate, and esomeprazole.

In some embodiments, a compound described herein, e.g., a compound of Formula (I), Formula (II), Formula (III), or Formula (IV) or a pharmaceutically acceptable salt thereof, can be used in combination with an anti-microbial agent. In some aspects of these embodiments, the anti-microbial agent is an anti-microbial peptide. In some aspects of these embodiments, the anti-microbial peptide is a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP 18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), or drosomycin (e.g., from fruit flies).

In some embodiments, the antibiotic is selected from the quinolone class of antibiotic compounds. In some aspects of these embodiments, the antibiotic is selected from the group consisting of levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

In some embodiments, the antibiotic is selected from the β-lactam class of antibiotic compounds.

In some embodiments, the antibiotic is selected from the cephalosporin class of antibiotic compounds. In some aspects of these embodiments, the antibiotic is selected from the group consisting of cefazolin, cefuroxime, ceftazidime, cephalexin, cephaloridine, cefamandole, cefsulodin, cefonicid, cefoperazine, cefoprozil, and ceftriaxone.

In some embodiments, the antibiotic is selected from the penicillin class of antibiotic compounds. In some aspects of these embodiments, the antibiotic is selected from the group consisting of penicillin G, penicillin V, procaine penicillin, and benzathine penicillin, ampicillin, and amoxicillin, benzylpenicillin, phenoxymethylpenicillin, oxacillin, methicillin, dicloxaciUin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

In some embodiments, the antibiotic is selected from the carbapenem class of antibiotic compounds. In some aspects of these embodiments, the antibiotic is selected from the group consisting of thienamycin, tomopenem, lenapenem, tebipenem, razupenem, imipenem, meropenem, ertapenem, doripenem, panipenem (betamipron), and biapenem.

In some embodiments, the antibiotic is selected from the lipopeptide class of antibiotic compounds. In some aspects of these embodiments, the antibiotic is selected from the group consisting of polymyxin B, colistin (polymyxin E), and daptomycin.

In some embodiments, the antibiotic is selected from the aminoglycoside class of antibiotic compounds. In some aspects of these embodiments, the antibiotic is selected from the group consisting of gentamicin, amikacin, tobramycin, debekacin, kanamycin, neomycin, netilmicin, paromomycin, sisomycin, spectinomycin, and streptomycin.

In some embodiments, the antibiotic is selected from the glycopeptide class of antibiotic compounds. In some aspects of these embodiments, the antibiotic is selected from the group consisting of vancomycin, teicoplanin, telavancin, ramoplanin, daptomycin, decaplanin, and bleomycin.

In some embodiments, the antibiotic is selected from the macrolide class of antibiotic compounds. In some aspects of these embodiments, the antibiotic is selected from the group consisting of azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

In some embodiments, the antibiotic is selected from the ansamycin class of antibiotic compounds. In some aspects of these embodiments, the antibiotic is selected from the group consisting of streptovaricin, geldanamycin, herbimycin, rifamycin, rifampin, rifabutin, rifapentine and rifamixin.

In some embodiments, the antibiotic is selected from the sulfonamide class of antibiotic compounds. In some aspects of these embodiments, the antibiotic is selected from the group consisting of sulfanilamide, sulfacetamide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

In some embodiments, the antibiotic is selected from the group consisting of quinolones, fluoroquinolones, β-lactams, cephalosporins, penicillins, carbapenems, lipopeptide antibiotics, glycopeptides, macrolides, ansamycins, sulfonamides, and combinations of two or more thereof.

In some embodiments, a compound described herein, e.g., a compound of Formula (I), Formula (II), Formula (III), or Formula (IV) or a pharmaceutically acceptable salt thereof, can be used in combination with an antifungal.

In some embodiments, the antifungal is selected from the polyene class of antifungal compounds. In some aspects of these embodiments, the antifungal is selected from the group consisting from Amphotericin B, Candicidin, Filipin, Hamycin, Natamycin, Nystatin, and Rimocidin.

In some embodiments, the antifungal is selected from the imidazole class of antifungal compounds. In some aspects of these embodiments, the antifungal is selected from the group consisting of Butoconazole, Clotrimazole, Econazole, Fenticonazole, Isoconazole, Ketoconazole, Luliconazole, Miconazole, Omoconazole, Oxiconazole, Sertaconazole, Sulconazole, and Tioconazole.

In some embodiments, the antifungal is selected from triazole class of antifungal compounds. In some aspects of these embodiments, the antifungal is selected from the group consisting of Albaconazole, Efinaconazole, Epoxiconazole, Fluconazole, Isavuconazole, Itraconazole, Posaconazole, Propiconazole, Ravuconazole, Terconazole, and Voriconazole.

In some embodiments, the antifungal is selected from thiazole class of antifungal compounds. In some aspects of these embodiments, the antifungal is Abafungin.

In some embodiments, the antifungal is selected from Allylamine class of antifungal compounds.

In some embodiments, the antifungal is selected from Echinocandin class of antifungal compounds. In some aspects of these embodiments, the antifungal is selected from the group consisting of anidulafungin, caspofungin, and micafungin.

In some embodiments, the antifungal is selected from the group consisting of a polyene, an imidazole, a triazole, a thiazole, an allylamine, a thiocarbamate, an echinocandin, and combinations of two or more thereof.

In some embodiments, the antifungal is fluconazole.

In some embodiments, the present application provides separate dosage forms of a compound described herein, e.g., a compound of Formula (I), Formula (II), Formula (III), or Formula (IV), or a pharmaceutically acceptable salt thereof and one or more of any of the above-described second agents, wherein the compound and second agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In some embodiments, the present disclosure is directed to a pharmaceutical composition comprising:
(i) a compound described herein, e.g., a compound of Formula (I), Formula (II), Formula (III), or Formula (IV) or a pharmaceutically acceptable salt thereof,
(ii) at least one additional agent (e.g., any one of agents described herein, for example aminoglycoside antibiotic such as gentamicin and cationic antimicrobial peptide such as defensin 1), and
(iii) a pharmaceutically acceptable carrier as described herein.

In some embodiments, the present disclosure is directed to a pharmaceutical composition comprising:
(i) a compound described herein, e.g., a compound of Formula (I), Formula (II), Formula (III), or Formula (IV) or a pharmaceutically acceptable salt thereof:
(ii) at least one additional agent (e.g., an antifungal such as a polyene, an imidazole, a triazole, a thiazole, an allylamine, a thiocarbamate, or echinocandin; e.g., antifungal is amphotericin B or fluconazole), and
(iii) a pharmaceutically acceptable carrier as described herein.

Some of the second agents referenced above will act synergistically with the compounds of the present application. In some embodiments, some of the second agents referenced above will show additive effect. When this occurs, it will allow the effective dosage of the second agent and/or the compound of the present application to be reduced from that required in a monotherapy. This has the advantage of minimizing toxic side effects of either the second agent of a compound of the present application, synergistic improvements in efficacy, improved ease of administration or use and/or reduced overall expense of compound preparation or formulation.

Methods of Administration

The compounds and compositions described herein (e.g., a compound of Formula (I), Formula (II), Formula (III), or Formula (IV) or a pharmaceutically acceptable salt thereof or a composition comprising a compound of Formula (I), Formula (II), Formula (III), or Formula (IV) or a pharmaceutically acceptable salt thereof) can be administered to a subject in a variety of ways. Exemplary methods of administration are described herein.

The compounds and compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. The methods and compositions of the described invention may be used in the form of drops or sprays (e.g., a nasal spray, aerosol spray, or pump spray) or other vehicles for inhalation or nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention formulated for inhalation or intranasal administration, can also be provided as solutions, suspensions, or viscous compositions. In some embodiments, the compositions of the invention (e.g., compositions of compounds described herein), are provided as solution compositions. In some embodiments, the compositions of the described invention can be delivered by other instruments, e.g., including but not limited to, a nebulizer, an insufflators, an inhaler, or a puffer.

The compounds and compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compounds and compositions of this invention may also be administered rectally, for example in the form of suppositories or enema for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compounds and compositions of this invention is useful when the desired treatment involves areas or organs readily accessible by topical application. For application topically to the skin, the compounds and compositions should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the compounds and compositions can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compounds and compositions of this invention may also be topically applied to the lower intestinal tract by rectal suppository formulation or in a suitable enema formulation. Topically-transdermal patches are also included in this invention.

When the compounds and compositions described herein can include one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds and compositions described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.02 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the compounds and compositions of this invention will be administered from about 1 to about 6 times per day or alternatively, as a continuous infusion.

Such administration can be used as a chronic or acute therapy. In some embodiments, a compound or composition described herein can be administered in a single dose per day. In some embodiments, a compound or composition described herein can be administered in a single dose per day. In some embodiments, a compound or composition described herein can be administered in a multiple doses per day. In some embodiments, a compound or composition described herein can be administered for about 1, 2, 3, 4, 5, 6, 7, 8, 9, or 10 days. In some embodiments, a compound or composition described herein can be administered for about 1, 2, 3, 4, 5, 6, 7, 8, 9, or 10 weeks. In some embodiments, a compound or composition described herein can be administered for about 1, 2, 3, 4, 5, 6, 7, 8, 9, or 10 months. In some embodiments, administration can occur 1, 2, or 3 days after clearance of an infection. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

A compound described herein (e.g., a compound of Formula (I) or a pharmaceutically acceptable salt thereof) or composition described herein (e.g., a composition comprising a compound of Formula (I), Formula (II), Formula (III), or Formula (IV) or a pharmaceutically acceptable salt thereof) can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). Preferred doses, dosage forms, or modes of administration are parenteral, e.g., intravenous, intramuscular, subcutaneous, intraparenteral, bucosal, sublingual, intraoccular, and topical. In another embodiment, the informational material can include instructions to administer the compound described herein to a suitable subject, e.g., a human, e.g., a human having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein such as the compound of Formula (I) as defined herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable delivery device.

Pharmaceutical Compositions

The compounds described herein (e.g., a compound of Formula (I) or a pharmaceutically acceptable salt thereof) can be formulated in a variety of manners, including for oral, or topical delivery (e.g., administered orally, parenterally, by inhalation spray, nebulizer, topically, rectally, nasally, buccally). Inclusion in feed, water or an inhaled formulation is particularly desirable for use with animals.

The compounds described herein (e.g., a compound of Formula (I), Formula (II), Formula (III), or Formula (IV) or a pharmaceutically acceptable salt thereof) can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The methods herein contemplate administration of an effective amount of compound or compound composition to achieve the desired or stated effect. Typically, the pharmaceutical compositions of this invention will be administered from about 1 to about 6 times per day. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof, an additional compound including for example, a steroid or an analgesic; and any pharmaceutically acceptable carrier, adjuvant or vehicle. Alternate compositions of this invention comprise a compound described herein or a pharmaceutically acceptable salt thereof, and a pharmaceutically acceptable carrier, adjuvant or vehicle. The compositions delineated herein include the compounds described herein, as well as additional therapeutic compounds if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 µm to about 50 µm (e.g., from about 0.1 µm to about 10 µm, or from about 0.2 µm to about 5 µm. In some embodiments, the composition includes a dispersion of suitably-sized dry particles, for example, precipitants or crystals) or a dispersion of a solution (e.g., droplets) of a suitable size.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of compounds described herein, both the compounds are generally present at dosage levels of between about 1 to 100%, and more preferably between about 5 to 95% of the dosage normally administered in a monotherapy regimen. Additionally, combinations of a plurality of compounds described herein are also envisioned. The compounds may be administered separately, as part of a multiple dose regimen, from the compounds of this invention. Alternatively, those compounds may be part of a single dosage form, mixed together with the compounds of this invention in a single composition.

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_2$-10 alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH═CH—) and propenylene (e.g., —CH═CHCH$_2$—, —CH$_2$—CH═CH—). Exemplary substituted alkenylene groups, e.g., substituted with one or more alkyl (methyl) groups, include but are not limited to, substituted ethylene (—C(CH$_3$)═CH—, —CH═C(CH$_3$)—), substituted propylene (e.g., —C(CH$_3$)═CHCH$_2$—, —CH═C(CH$_3$)CH$_2$—, —CH═CHCH(CH$_3$)—, —CH═CHC(CH$_3$)$_2$—, —CH(CH$_3$)—CH═CH—, —C(CH$_3$)$_2$—CH═CH—, —CH$_2$—C(CH$_3$)═CH—, —CH$_2$—CH═C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("hetero$C_2$-10 alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_{1-8}$ alkyl, C$_{1-8}$ haloalkyl, cyano, hydroxy, C$_{1-8}$ alkoxy, and amino.

Examples of representative substituted aryls include the following

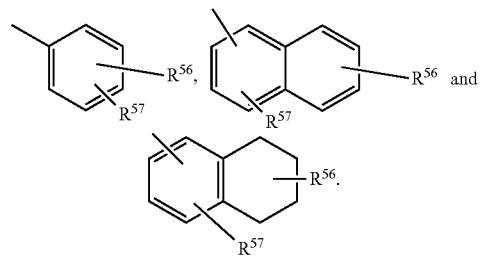

wherein one of R$^{56}$ and R$^{57}$ may be hydrogen and at least one of R$^{16}$ and R$^{57}$ is each independently selected from C$_{1-8}$ alkyl, C$_{1-8}$ haloalkyl, 4-10 membered heterocyclyl, alkanoyl, C$_{1-8}$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO₂alkyl, Saryl, SOaryl, SO₂aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_{1-8}$ alkyl, $C_{1-4}$haloalkyl, $C_{3-10}$ cycloalkyl, 4-10 membered heterocyclyl, $C_{6-10}$ aryl, substituted $C_{6-10}$ aryl, 5-10 membered heteroaryl, or substituted 5-10 membered heteroaryl.

Other representative aryl groups having a fused heterocyclyl group include the following:

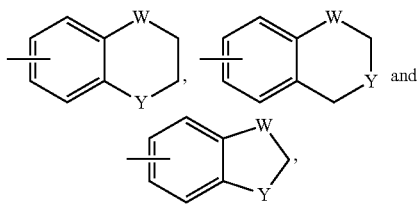

wherein each W is selected from $C(R^{66})_2$, $NR^{66}$, O, and S; and each Y is selected from carbonyl, $NR^{66}$, O and S; and $R^{66}$ is independently hydrogen, $C_{1-8}$ alkyl, $C_{3-10}$ cycloalkyl, 4-10 membered heterocyclyl, $C_{6-10}$ aryl, and 5-10 membered heteroaryl.

"Fused aryl" refers to an aryl having two of its ring carbons in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

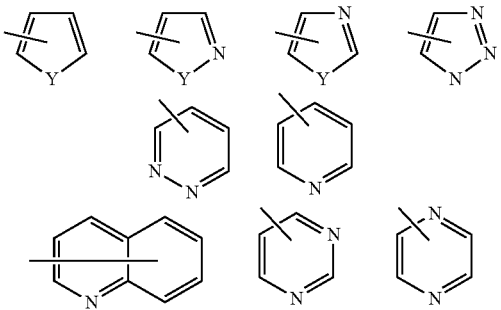

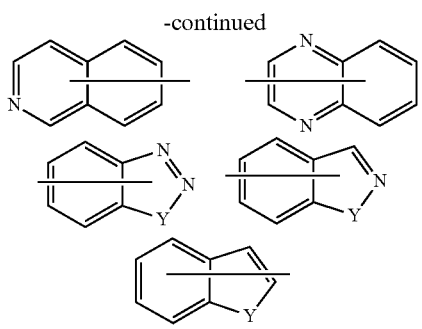

wherein each Y is selected from carbonyl, N, NR$^{65}$, O, and S; and R$^{65}$ is independently hydrogen, C$_{1-8}$ alkyl, C$_{3-10}$ cycloalkyl, 4-10 membered heterocyclyl, C$_{6-10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" or "cycloalkyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

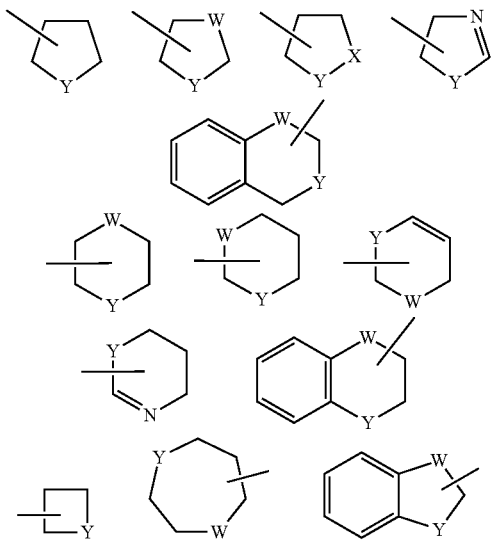

wherein each W is selected from $CR^{67}$, $C(R^{67})_2$, $NR^{67}$, O, and S; and each Y is selected from $NR^{67}$, O, and S; and $R^{67}$ is independently hydrogen, $C_{1-8}$ alkyl, $C_{3-10}$ cycloalkyl, 4-10 membered heterocyclyl, $C_{6-10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g,. heteroaryl, cycloalkenyl, e.g,. cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstitued alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)— $C_{1-8}$ alkyl, —C(O)—(CH$_2$)$_t$($C_{6-10}$ aryl), —C(O)—(CH$_2$)$_t$(5-10 membered heteroaryl), —C(O)—(CH$_2$)$_t$($C_{3-10}$ cycloalkyl), and —C(O)—(CH$_2$)$_t$(4-10 membered heterocyclyl), wherein t is an integer from 0 to 4. In certain embodiments, $R^{21}$ is $C_{1-8}$ alkyl, substituted with halo or hydroxy; or $C_{3-10}$ cycloalkyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Acylamino" refers to a radical —NR$^{22}$C(O)R$^{23}$, where each instance of $R^{22}$ and $R^{23}$ is independently hydrogen, substituted or unsubstitued alkyl, substituted or unsubstituted alkenyl, substituted or unsubstituted alkynyl, substituted or unsubstitued carbocyclyl, substituted or unsubstituted heterocyclyl, substituted or unsubstituted aryl, or substituted or unsubstitued heteroaryl,, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)— $C_{1-8}$ alkyl, —NR$^{24}$C(O)—(CH$_2$)$_t$($C_{6-10}$ aryl), —NR$^{24}$C(O)—(CH$_2$)$_t$(5-10 membered heteroaryl), —NR$^{24}$C(O)—(CH$_2$)$_t$($C_{3-10}$ cycloalkyl), and —NR$^{24}$C(O)—(CH$_2$)$_t$(4-10 membered heterocyclyl), wherein t is an integer from 0 to 4, and each $R^{24}$ independently represents H or $C_{1-8}$ alkyl. In certain embodiments, $R^{25}$ is H, $C_{1-8}$ alkyl, substituted with halo or hydroxy; $C_{3-10}$ cycloalkyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy; and $R^{26}$ is H, $C_{1-8}$ alkyl, substituted with halo or hydroxy; $C_{3-10}$ cycloalkyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxyl; provided at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, or substituted or unsubstitued heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_{1-8}$ alkyl, substituted with halo or hydroxy; $C_{3-10}$ cycloalkyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstitued carbocyclyl, substituted or unsubstituted heterocyclyl, substituted or unsubstituted aryl, or substituted or unsubstitued heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_{6-10}$ aryl, aryloxy, carboxyl, cyano, $C_{3-10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_{6-10}$ aryl), —O—(CH$_2$)$_t$(5-10 membered heteroaryl), —O—(CH$_2$)$_t$(C$_{3-10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_{1-8}$ alkyl, $C_{3-8}$ alkenyl, $C_{3-8}$ alkynyl, $C_{6-10}$ aryl, 5-10 membered heteroaryl, 4-10 membered heterocyclyl, or $C_{3-10}$ cycloalkyl; or $C_{1-8}$ alkyl, substituted with halo or hydroxy; $C_{3-8}$ alkenyl, substituted with halo or hydroxy; $C_{3-8}$ alkynyl, substituted with halo or hydroxy, or —(CH$_2$)$_t$(C$_{6-10}$ aryl), —(CH$_2$)$_t$(5-10 membered heteroaryl), —(CH$_2$)$_t$(C$_{3-10}$ cycloalkyl), or —(CH$_2$)$_t$(4-10 membered heterocyclyl), wherein t is an integer between 0 and 8, each of which is substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy; or both $R^{38}$ groups are joined to form an alkylene group.

Exemplary "substituted amino" groups include, but are not limited to, —NR$^{39}$—$C_{1-8}$ alkyl, —NR$^{39}$—(CH$_2$)$_t$(C$_{6-10}$ aryl), —NR$^{39}$—(CH$_2$)$_t$(5-10 membered heteroaryl), —NR$^{39}$—(CH$_2$)$_t$(C$_{3-10}$ cycloalkyl), and —NR$^{39}$—(CH$_2$)$_t$(4-10 membered heterocyclyl), wherein t is an integer from 0 to 4, for instance 1 or 2, each $R^{39}$ independently represents H or $C_{1-8}$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both mono-substituted amino and disubstituted amino groups.

"Azido" refers to the radical —N$_3$.

"Oxo" refers to =O.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_{1-8}$ alkyl, $C_{3-10}$ cycloalkyl, 4-10 membered heterocyclyl, $C_{6-10}$ aryl, aralkyl, 5-10 membered heteroaryl, and heteroaralkyl; or $C_{1-8}$ alkyl substituted with halo or hydroxy; or $C_{3-10}$ cycloalkyl, 4-10 membered heterocyclyl, $C_{6-10}$ aryl, aralkyl, 5-10 membered heteroaryl, or heteroaralkyl, each of which is substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy; provided that at least one $R^{62}$ is other than H.

Exemplary "substituted carbamoyl" groups include, but are not limited to, —C(O) NR$^{64}$—$C_{1-8}$ alkyl, —C(O)NR$^{64}$—(CH$_2$)$_t$(C$_{6-10}$ aryl), —C(O)N$^{64}$—(CH$_2$)$_t$(5-10 membered heteroaryl), —C(O)NR$^{64}$—(CH$_2$)$_t$(C$_{3-10}$ cycloalkyl), and —C(O)NR$^{64}$—(CH$_2$)$_t$(4-10 membered heterocyclyl), wherein t is an integer from 0 to 4, each $R^{64}$ independently represents H or $C_{1-8}$ alkyl and any aryl, heteroaryl, cycloalkyl or heterocyclyl groups present, may themselves be substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethylene" refers to substituted or unsubstituted —(C—C)—.

"Ethenyl" refers to substituted or unsubstituted —(C=C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NRb)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(O)R$^{aa}$, e.g., —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rad groups; each instance of R$^{bb}$ is, independently, selected from hydrogen, —OH, —OR$^{1a}$, —N(R')$_2$, —CN, —C(=O)R$^{aa}$, —C(=O)N(R)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ee}$)$_2$, —NR$^{ff}$(=O)R$^{ee}$, —NR$^{ee}$MCO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$Re$^{ee}$, —SO$_2$N(R$^{ff}$)$_2$, —SO$_2$R$^{ee}$, —SO$_2$OR$^{ee}$, —OSO$_2$R$^{ee}$, —S(O)R$^{ee}$, e.g., —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups; each instance of R$^f$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^f$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, SO$_4$$^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$_4$$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein. In some embodiments, the disease is an infection caused by a bacterium.

"*Helicobacter pylori*" and "*H. pylori*" are used interchangeably herein.

In an embodiment, the methods provided herein can be used to treat an nosocomial infection caused by *H. pylori*. As used herein, a "nosocomial infection" refers to an infection which is a result of treatment in a hospital or a healthcare service unit, but secondary to the patient's original condition. Infections are considered nosocomial if they first appear 48 hours or more after hospital admission or within 30 days after discharge. This type of infection is also known as a hospital-acquired infection (or more generically a healthcare-associated infections).

In an embodiment, the methods provided herein can be used to treat a community-acquired infection caused by *H. pylori*. As used herein, a "community-acquired infection" refers also to an infection which is a result of activity in a highly populated facility or area. Any infection acquired in the community, that is, contrasted with those acquired in a health care facility (i.e., a nosocomial infection). An infection would be classified as community-acquired if the patient had not recently been in a health care facility or been in contact with someone who had been recently in a health care facility.

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject.

As used herein, the term "treat" or "treatment" is defined as the application or administration of a compound to a subject, e.g., a patient, or application or administration of the compound to an isolated tissue or cell, e.g., cell line, from a subject, e.g., a patient, who has a bacterial infection (e.g., a bacterial described herein) or a bacterial infection, with the purpose to cure, heal, alleviate, relieve, alter, remedy, ameliorate, improve or affect the bacterial infection, one or more symptoms of the bacterial infection or the predisposition toward the bacterial infection (e.g., to prevent at least one symptom of the bacterial infection or to delay onset of at least one symptom of the bacterial infection).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a bacterial infection, or a "a prophylactically effective amount" of the compound refers to an amount effective, upon single- or multiple-dose administration to the subject, in preventing or delaying the occurrence of the onset or recurrence of a disorder or a symptom of the bacterial infection.

As used herein, a "minimum inhibitory concentration (MIC)" is the lowest concentration of an anti-bacterial that inhibits the visible growth of a bacterium after overnight incubation. MIC can be used to confirm resistance of bacteria to an anti-bacterial agent and also to monitor the activity of new anti-bacterial agents. MIC can be determined by agar or broth dilution methods usually following the guidelines of a reference body such as the Clinical and Laboratory Standards Institute (CLSI), British Society for Antimicrobial Chemotherapy (BSAC) or The European Committee on Antimicrobial Susceptibility Testing (EU-CAST). Methods to determine MIC are described, e.g., in Andrews J M. *Journal of Antimicrobial Chemotherapy* 48 (Suppl. 1):5-16, (2001).

As used herein, "multiple drug resistance (MDR)" (also called multidrug resistance) is a condition enabling a disease-causing organism, e.g., bacteria, to no longer be killed or inhibited in growth by distinct drugs or chemicals, e.g., anti-bacterial agents in doses that are considered clinically relevent. A bacterium exhibiting MDR may also be referred to herein as a "multidrug-resistant" bacterium.

As used herein, "resistant microorganism or bacterium" means an organism which has become resistant to an anti-bacterial agent. In embodiments the minimum inhibitory concentration of a resistant bacterium will be at least, 2, 5, 10, or 100 greater than for that seen with a non-resistant bacterium for a selected anti-bacterial agent.

As used herein, "resistance breakpoint" is the threshhold concentration of an antibacterial agent above which a bacterium is considered resistant as defined above.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Abbreviations

ACN: acetonitrile
AGS: gastric adenocarcinoma cell lines
CHO: chinese hamster ovary cells
CFU: colony-forming unit
DCM: dichloromethane (also known as methylene chloride)
DMEM: dulbecco's modified eagle medium
DMSO: dimethyl sulfoxide
$EC_{50}$: the concentration of a drug that gives half-maximal response
EDAC: 1-ethyl-3-(3-dimethylaminopropyl)carbodiimide
EtOAc: ethyl acetate
FBS: fetal bovine serum
FICI: fractional inhibitory concentration index
HCl: hydrochloric acid
HOBT: hydroxybenzotriazole
HPLC-DAD-MS: high performance liquid chromatography with diode array detector coupled with mass spectrometry
$OD_{600}$: Optical density measured at a wavelength of 600 nm
MeOH: methanol MgSO₄: magnesium sulfate
MHB: mycorrhiza helper bacteria
MIC: minimum inhibitory concentration
MLC: minimum lethal concentration
MBC: minimum bactericidal concentration. Also called minimum lethal concentration (MLC).
mp: Melting point
MOI: multiplicity of infection
NMR: nuclear magnetic resonance spectroscopy
NUAG: neutralizer agar
PBS: phosphate-buffered saline
PPI: proton pump inhibitors
RT: room temperature
TEA: trimethylamine
THF: tetrahydrofuran
WST-1: 2-(4-iodophenyl)-3-(4-nitrophenyl)-5-(2,4-disulfophenyl)-2H-tetrazolium
ZOI: zone of inhibition Example 1. Preparation of Exemplary Compounds Synthesis of phosphoranildohydrazones of 5-nitro-2-furaldehyde (Scheme 1)

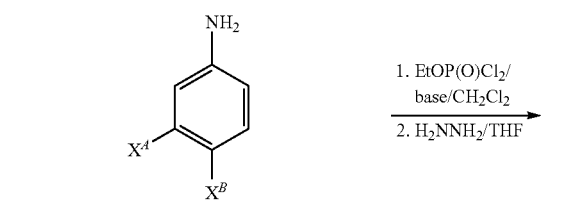

Compound C1 ($X^A$ = ——H; $X^B$ = ——H)
Compound B1 ($X^A$ = ——H; $X^B$ = ——CH₃)
Compound A1 ($X^A$ = ——H; $X^B$ = ——OCH₃)
Compound D1 ($X^A$ = ——H; $X^B$ = ——Cl)
Compound E1 ($X^A$ = ——Cl; $X^B$ = ——Cl)

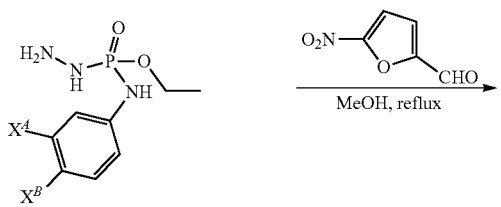

Compound C2 ($X^A$ = ——H; $X^B$ = ——H)
Compound B2 ($X^A$ = ——H; $X^B$ = ——CH₃)
Compound A2 ($X^A$ = ——H; $X^B$ = ——OCH₃)
Compound D2 ($X^A$ = ——H; $X^B$ = ——Cl)
Compound E2 ($X^A$ = ——Cl; $X^B$ = ——Cl)

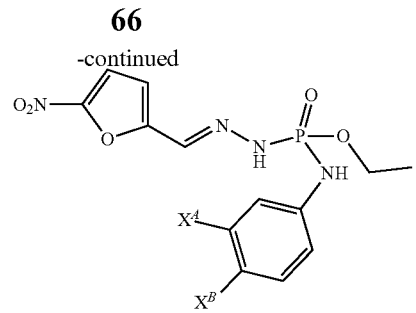

Compound 1 ($X^A$ = ——H; $X^B$ = ——H)
Compound 2 ($X^A$ = ——H; $X^B$ = ——CH₃)
Compound 3 ($X^A$ = ——H; $X^B$ = ——OCH₃)
Compound 4 ($X^A$ = ——H; $X^B$ = ——Cl)
Compound 5 ($X^A$ = ——Cl; $X^B$ = ——Cl)

Synthesis of hydrazides (Compound A2, Compound B2, Compound C₂, Compound D2, and Compound E2)

Method A: A solution of Compound A1, Compound B1, Compound C₁, Compound D1, or Compound E1 in dichloromethane (DCM) (1 mL/mmol) containing triethylamine (TEA) (1 equivalent) is added dropwise to an equimolar solution of ethyl dichlorophosphate in DCM stirred at RT. After ~18 h, the reaction mixture is concentrated and the residue is treated with tetrahydrofuran (THF) (1 mL/mmol), then vacuum filtered to remove TEA HCl. The filtrate is added dropwise to a mixture of hydrazine hydrate (4 equivalents) in an equal volume of THF stirred at 0° C. Stirring is continued overnight at room temperature, after which the lower phase of the reaction mixture is discarded, and the THF solution is concentrated. The crude hydrazide product (Compound A2, Compound B2, Compound C₂, Compound D2, or Compound E2) is triturated with ether, washed with water, as necessary, and used directly in the next step without further purification.

Method B: A solution of Compound A1, Compound B1, Compound C₁, Compound D1, or Compound E1 (2 equivalents) in THF (0.5 mL/mmol) is added dropwise to solution of ethyl dichlorophosphate (1 equivalent) in THF (1 mL/mmol) stirred at RT. After 18 h, the reaction mixture is vacuum filtered and the filter cake is washed with small portions of THF until washes are colorless. The filtrate is treated with hydrazine hydrate (4 equivalents) in one portion and the mixture is stirred for ~18 h. The lower phase of the reaction mixture is discarded, and the THF solution is concentrated. The crude hydrazide product (Compound A2, Compound B2, Compound C₂, Compound D2, or Compound E2) is triturated with ether, washed with water, as necessary, and used directly in the next step without further purification.

Synthesis of hydrazones (Compound 1, Compound 2, Compound 3, Compound 4, and Compound 5)

A mixture of hydrazide and equimolar 5-nitro-2-furaldehyde in MeOH (5 mL/mmol hydrazide) is stirred at reflux for 3 h. Solvent is removed under reduced pressure and the crude hydrazone is crystallized from a suitable solvent as described below (see "Methods of purification and characterization data for Compounds 1-5").

TABLE 2

Exemplary syntheses of hydrazides (Compounds A2-E2)
Syntheses of hydrazides: Compounds A1-E1

| Method | Compound Number | mmol | Hydrazide wt, g | % yield |
|---|---|---|---|---|
| A | C1 | 25 | 5.55 | 90 |
| A | C1 | 25 | 5.64 | 91 |
| B | E1 | 200 | 14.94 | 53 |
| A | B1 | 50 | 9.04 | 79 |
| B | B1 | 100 | 6.73 | 59 |
| A | D1 | 50 | 7.56 | 61 |
| A | A1 | 60 | 9.83 | 77 |

TABLE 3

Exemplary syntheses of Compounds 1-5
Synthesis of hydrazones: Compounds 1-5

| Hydrazide X | mmol | Hydrazone wt, g | % yield | mp, °C | Crystallization solvent |
|---|---|---|---|---|---|
| 4-OCH$_3$ | 43.6 | 14.64 | 91 (87)[a] | 99-104 | MeOH |
| 3,4-Cl$_2$ | 52.6 | 18.90 | 88 (85)[a] | 104-111 | CH$_3$CN-water |
| 4-CH$_3$ | 39 | 11.35 | 83 (81)[b] | 110-116 | MeOH-water |
| 4-Cl | 30 | 8.17 | 73 (71)[b] | 109-124 | CH$_3$CN-water |
| H | 45 | 10.94 | 72 (70)[b] | 132-137 | CH$_3$CN-water |

[a] as hydrate
[b] as hemihydrate

Methods of Purification and Characterization Data for Compound 1, Compound 2, Compound 3, Compound 4, and Compound 5

Compound 1: Purification by crystallization from CH$_3$CN-water gave a yellow solid [10.94 g, 53% yield (based on aniline)]; mp 132-137° C.; $^1$H NMR (400 MHz, DMSO-d$_6$) δ 10.224 (d, 1H, NH), 8.205 (d, 1H; NH), 7.880 (s, 1H, CH=N), 7.719 (d, J=4 Hz, 1H, furan), 7.193 (t, 2H, phenyl), 7.109 (m, 2H, phenyl), 6.994 (d, J=4 Hz, 1H, furan), 6.852 (m, 1H, phenyl), 4.103 (m, 2H, CH$_2$), 1.294 (t, 3H, CH$_3$); HPLC-DAD-MS: 98.7% (200 nm); m/z 339.0 [M+H]$^+$; 337.0 [M−H]$^−$; Calcd for C$_{13}$H$_{15}$N$_4$O$_5$P·1/2H$_2$O (347.26): C, 44.96; H, 4.64; N, 16.13. Found: C, 44.87; H, 4.63; N, 16.04.

Compound 2: Purification by crystallization from MeOH-water gave a yellow solid [11.35 g, 32% yield (based on p-toluidine)]; mp 110-116° C.; $^1$H NMR (400 MHz, DMSO-d$_6$) δ 10.176 (d, 1H, NH), 8.059 (d, 1H; NH), 7.866 (s, 1H, CH=N), 7.720 (d, J=4 Hz, 1H, furan), 6.9-7.1 (m, 4H, phenyl), 6.9-7.1 (d, J=4 Hz, 1H, furan), 4.084 (m, 2H, CH$_2$), 2.184 (s, 3H, CH$_3$), 1.294 (t, 3H, CH$_3$); HPLC-DAD-MS: 99.5% (200 nm); m/z 353.1 [M+H]$^+$; Calcd for C$_{14}$H$_{17}$N$_4$O$_5$P·1/2H$_2$O (361.29): C, 46.54; H, 5.02; N, 15.51. Found: C, 46.31; H, 5.03; N, 15.41.

Compound 3: Purification by crystallization from MeOH gave a yellow solid [14.64 g, 76% yield (based on anisidine)]; mp 99-104° C.; $^1$H NMR (400 MHz, DMSO-d$_6$) δ 10.135 (d, 1H, NH), 7.923 (d, 1H; NH), 7.862 (s, 1H, CH=N), 7.725 (d, J=4 Hz, 1H, furan), 7.033 (dd, J=4.8, 2 Hz, 2H, phenyl), 6.993 (d, J=4 Hz, 1H, furan), 6.789 (dd, J=4.8, 2 Hz, 2H, phenyl), 4.075 (m, 2H, CH$_2$), 3.666 (s, 3H, OCH$_3$), 1.278 (t, 3H, CH$_3$); HPLC-DAD-MS: 99.5% (200 nm); m/z 369.1 [M+H]$^+$; Calcd for C$_{14}$H$_{17}$N$_4$O$_6$P·H$_2$O (386.30): C, 43.53; H, 4.96; N, 14.50. Found: C, 43.67; H, 4.90; N, 14.40.

Compound 4: Purification by crystallization from CH$_3$CN-water gave a yellow solid [8.17 g, 43% yield (based on 4-chloroaniline)]; mp 109-124° C.; $^1$H NMR (400 MHz, DMSO-d$_6$) δ 10.253 (d, 1H, NH), 8.390 (d, 1H; NH), 7.878 (s, 1H, CH=N), 7.727 (d, J=4 Hz, 1H, furan), 7.253 (m, J=8.8 Hz, 2H, phenyl), 7.123 (m, J=8.8 Hz, 2H, phenyl), 7.011 (d, J=4 Hz, 1H, furan), 4.105 (m, 2H, CH$_2$), 1.295 (t, 3H, CH$_3$); HPLC-DAD-MS: 99.0% (200 nm); m/z 373.0 [M+H]$^+$; 370.9 [M−H]$^−$; Calcd for C$_{13}$H$_{14}$ClN$_4$O$_5$P·1/2H$_2$O (381.71): C, 40.91; H, 3.96; N, 14.68. Found: C, 40.98; H, 3.98; N, 14.67.

Compound 5: Purification by crystallization from CH$_3$CN-water gave a yellow solid [18.90 g, 45% yield (based on 3,4-dichloroaniline)]; mp 104-111° C.; $^1$H NMR (400 MHz, DMSO-d$_6$) δ 10.345 (broad, 1H, NH), 8.640 (broad, 1H; NH), 7.896 (d, J=0.8 Hz, 1H, CH=N), 7.736 (d, J=3.6 Hz, 1H, furan), 7.459 (d, J=9.2 Hz, 1H, phenyl), 7.345 (d, J=2.4 Hz, 1H, phenyl), 7.101 (dd, J=8.8, 2.4 Hz, 1H, phenyl), 7.032 (d, J=4 Hz, 1H, furan),, 4.131 (m, 2H, CH$_2$), 1.313 (t, 3H, CH$_3$); HPLC-DAD-MS: 99.2% (200 nm); m/z 406.9 [M+H]$^+$; 404.9 [M−H]$^−$; Calcd for C$_{13}$H$_{13}$Cl$_2$N$_4$O$_5$P·H$_2$O (425.16): C, 36.72; H, 3.56; N, 13.18. Found: C, 36.93; H, 3.51; N, 13.28.

Synthesis of Compound 13

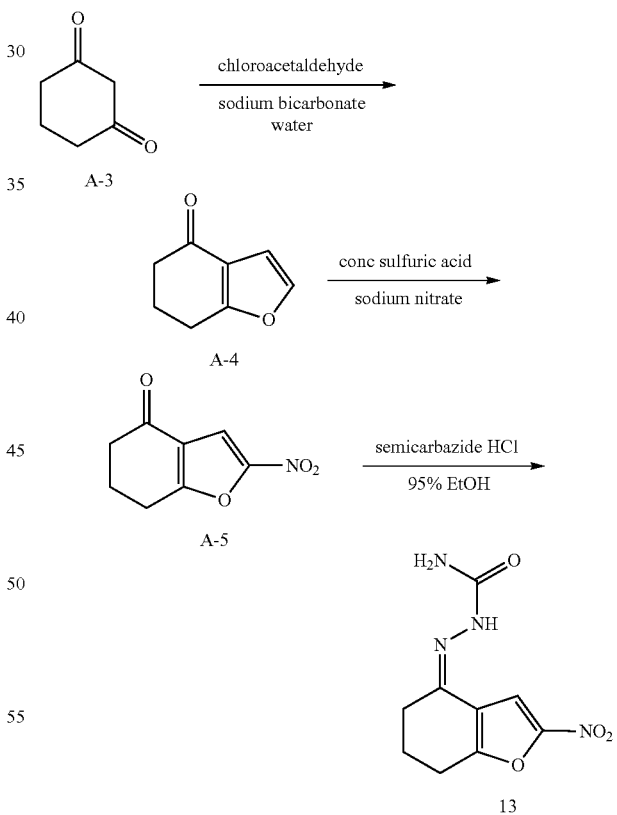

Step 1

A solution of 1,3-cyclohexanedione (A-3; 22.4 g, 200 mmol) in water (230 mL; Note 1) was added dropwise to a mixture of chloroacetaldehyde (40 mL, 40% in water, d 1.214, 247 mmol) in water (160 mL) containing sodium bicarbonate (20 g, 238 mmol) stirred at 0° C. After stirring 70 h at RT, the mixture was diluted with EtOAc (200 mL)

and pH was adjusted to −1 with conc sulfuric acid. After 1 hour, the aqueous phase was extracted with EtOAc and the combined extracts were dried (MgSO$_4$), filtered and concentrated to a syrup, which was purified by flash chromatography [hexane/EtOAc (4:1)] to accord A-4 as a solid (60% yield).

Step 2

6,7-Dihydro-5H-benzofuran-4-one (A-4) was nitrated using conc sulfuric acid (I mL/mmol substrate) and sodium nitrate (1 equivalent). The reaction mixture was poured over ice, and the crude product was isolated by vacuum filtration and crystallized from boiling water to give pure 2-nitro-6,7-dihydro-5H-benzofuran-4-one (A-5).

Step 3

An equimolar mixture of semicarbazide HCl and 2-nitro-6,7-dihydro-5H-benzofuran-4-one (A-5) in 95% of ethanol (12 mL/mmol) was heated at 80° C. for 1 hour. The precipitates from the cooled reaction mixture were filtered to give compound 13 as a solid (95%).

Synthesis of Compound 15

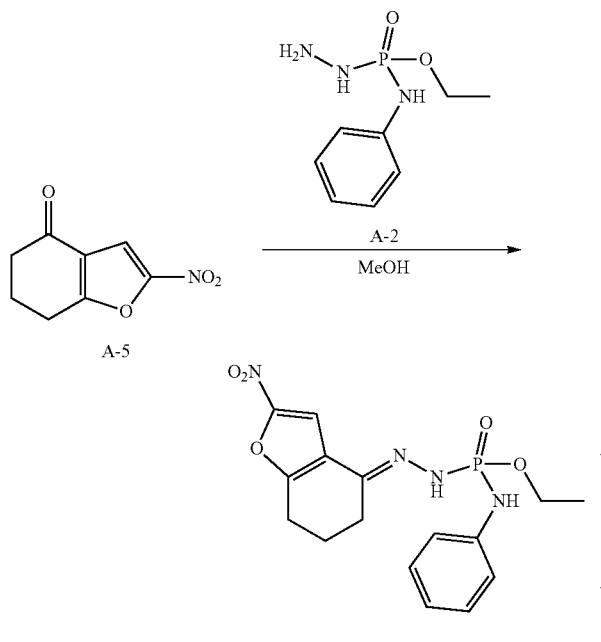

An equimolar mixture of 2-nitro-6,7-dihydro-5H-benzofuran-4-one (A-5) and A-2 in methanol (3 mL/mmol) was heated at 70° C. for 3 hours. The reaction mixture was concentrated, and the residue was titurated with water. The crude product was purified by flash chromatography to give compound 15 as a solid.

Synthesis of Compound 16

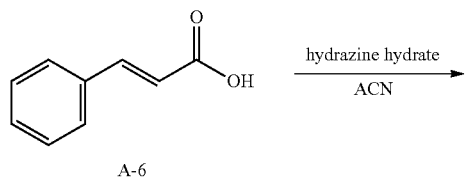

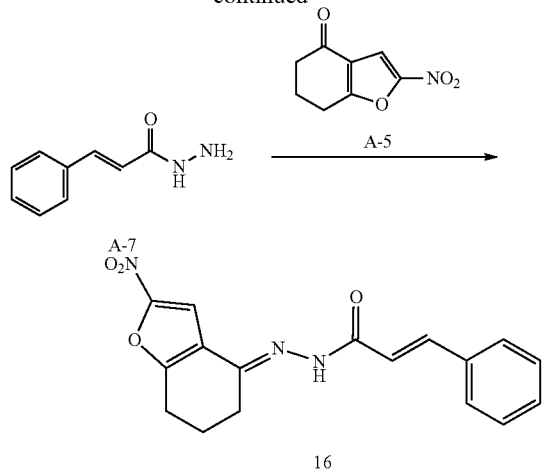

Step 1

A mixture of cinnamic acid (A-6) in ACN (2 mL/mmol) stirred at room temperature was treated with HOBT (1.2 equivalents), followed by EDAC HCl (1.2 equivalents). After stirring for 2.5 h, the mixture was added dropwise to a solution of hydrazine hydrate (2 equivalents) in an equal volume of ACN stirred at 0° C. After warming to 10° C., the reaction mixture was diluted with water and extracted with EtOAc. EtOAc extracts were washed with saturated sodium bicarbonate solution and concentrated to give cinnamic acid hydrazide (A-7) of adequate purity to be used in the next step.

Step 2

An equimolar mixture of A-7 and 2-nitro-6,7-dihydro-5H-benzofuran-4-one (A-5) in methanol (5 mL/mmol) was heated at 70° C. for 3 hours. The reaction mixture was concentrated and the residue was titurated with water. The precipitates from the cooled reaction mixture were filtered to give compound 16 as a solid.

Example 2. Preparation of Exemplary Compounds

Synthesis of additional compounds

Synthesis of Compound 17

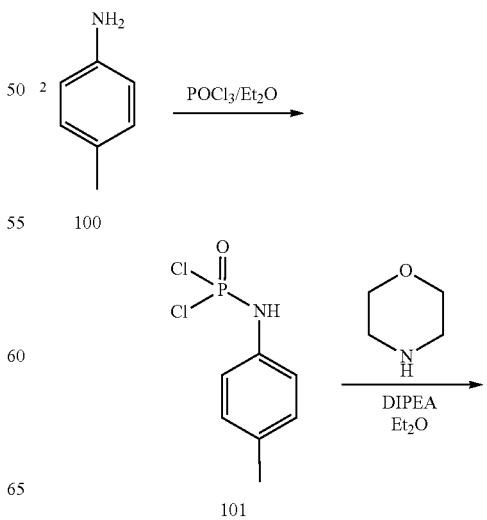

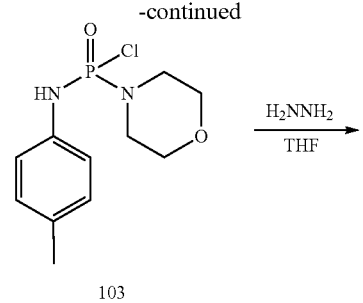

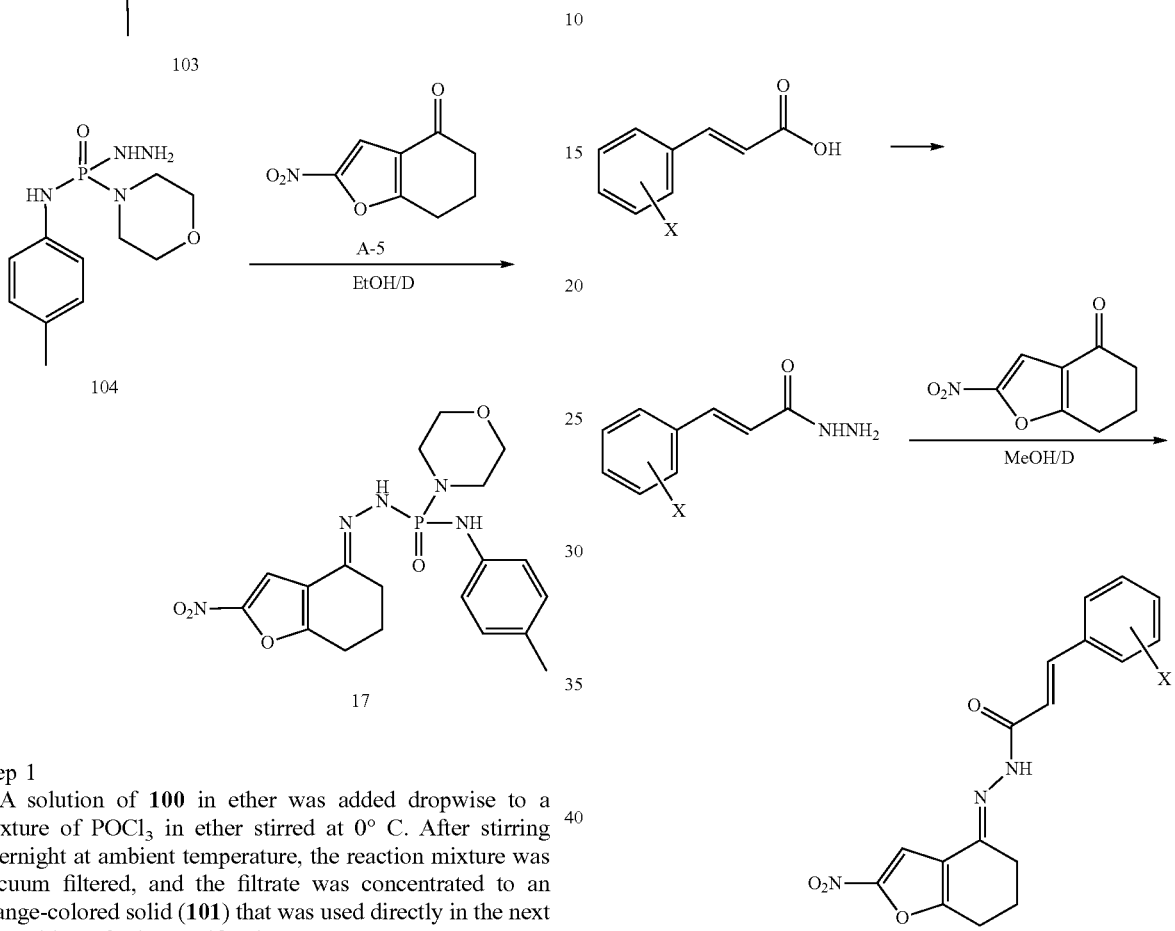

filtered, and the filtrate was concentrated to a semi-solid that was triturated with ether, dried, sonicated with a large volume of water, collected by vacuum filtration, washed with water and air-dried. The pure compound [17; >98% [UHPLC (210 nm)]; m/z 434.16425 (M+H)$^+$] was obtained by crystallization from 2-BuOH.

Synthesis of Compounds 18, 19, 20 and 21

X = 4-OCH$_3$ (18)
X = 4-Cl (19)
X = 4-NO$_2$ (20)
X = 3-OCH$_3$, 4-OH (21)

Step 1
A solution of 100 in ether was added dropwise to a mixture of POCl$_3$ in ether stirred at 0° C. After stirring overnight at ambient temperature, the reaction mixture was vacuum filtered, and the filtrate was concentrated to an orange-colored solid (101) that was used directly in the next step without further purification.

Step 2
A solution of morpholine and DIPEA in ether was added dropwise to a solution of 12 in ether stirred at 0° C. After stirring overnight at ambient temperature, the solvent was decanted from a residual solid and concentrated to a lightly colored solid (103) that was used directly in the next step without further purification.

Step 3
A solution of 103 in THF was added dropwise to a mixture of hydrazine hydrate in THF stirred at 0° C. After stirring overnight at ambient temperature, the reaction mixture was vacuum filtered, and the filtrate was concentrated to a syrup that was partitioned between EtOAc-water. The organic phase was washed with water, and the combined aqueous phases were concentrated to dryness, sonicated with THF, and vacuum filtered (Celite). The filtrate was concentrated to a syrup that was taken up in EtOAc, treated with MgSO$_4$ and activated charcoal, vacuum filtered (Celite) and concentrated to a hard, yellow foam (104).

A mixture of 104 and 2-nitro-6,7-dihydro-5H-benzofuran-4-one (A-5) in EtOH was stirred at reflux for ~4 h. After cooling to RT, the reaction mixture was vacuum A mixture of substituted cinnamic acid in ACN stirred at room temperature was treated with HOBT (1.2 equivalents), followed by EDAC (1.2 equivalents). After stirring for 4-5 h, the mixture was added dropwise to a mixture of hydrazine hydrate (10 equivalents) in ACN stirred at 0° C. The reaction mixture was stored in the freezer overnight. The solvents were decanted, and the residual solid was sonicated with saturated NaHCO$_3$, collected by vacuum filtration, washed with saturated NaHCO$_3$, washed with water and air-dried. The hydrazide was pure enough to use directly in the next step.

An equimolar mixture of hydrazide from step 1) and 2-nitro-6,7-dihydro-5H-benzofuran-4-one (A-5) in methanol was heated at reflux for 3 hours. Upon cooling, the product precipitated from solution, was collected by vacuum filtration, washed with MeOH and air-dried:

| Compound | yield | UHPLC (210 nm) | m/z (M + H)+ |
|---|---|---|---|
| 18 | 77% | >97% | 356.12459 |
| 19 | 75% | >91% * | 360.07476 |
| 20 | 63% | >95% | 371.09989 |
| 21 | 69% | na | |

* Crystallization from hot ACN improved purity

Example 3. Determination of MIC and MBC Concentration Against H. pylori for Exemplary Compounds The MIC and MBC of the compounds can be measured with the following procedure: In vitro antibacterial activity was tested using the broth microdilution assay. Experiments were carried out in triplicate using Müller-Hinton broth supplemented with 10% FBS in 96-well plates at a total assay volume of 100 µL. Antimicrobials were tested against H. pylori. Two-fold serial dilutions were prepared between the concentration range 0.01-64 µg/mL. An initial bacterial inoculum was adjusted to $OD_{600}=0.06$ and incubated with test compounds at 37° C. for 3 days in humidified incubators under the 5% $CO_2$ atmosphere. $OD_{600}$ was measured and the lowest concentration of compound that inhibited bacterial growth was reported as the MIC. See Gwisai T, et al. Repurposing niclosamide as a versatile antimicrobial surface coating against device-associated, hospital-acquired bacterial infections. Biomed Mater. 2017; 12(4):045010. The pH was adjusted to acidic condition with 1 N HCL. The minimal bactericidal concentration (MBC) was determined by plating 5 µL of broth culture from the MIC assay onto Müller-Hinton agar (BD Biosciences) supplemented with 10% FBS. After 72 h, the lowest concentration at which colonies were not observed was reported as the MBC.

MIC and MBC data for exemplary compounds based on the above MIC and MBC procedures are shown in Table 4.

TABLE 4

MIC and MBC data for exemplary compounds against H. pylori.

| Compound No. | MIC (µg/mL) | MBC (µg/mL) |
|---|---|---|
| 1 | 1-2 | 2 |
| 2 | 2 | 2 |
| 3 | 2 | 2 |
| 4 | 1 | 1 |
| 5 | 1 | 1 |
| 6 | 2 | 2 |
| 7 | 2 | 2 |
| 8 | 4 | 4 |
| 9 | 4 | 4 |
| 10 | 4 | 4 |
| 11 | 1 | 1 |
| 12 | 1 | 1 |
| 13 | 0.25 | 0.25 |
| 14 | 4 | 4 |
| 15 | 0.25 | 0.25 |
| 16 | 0.25 | 0.25 |
| Niclosamide | 0.25 | 0.5 |
| Amoxicillin | 0.01 | 0.025 |

Example 4. MIC with Different Strains

MIC data with different strains of H. pylori is shown in Table 5.

TABLE 5

MIC data for exemplary compounds, identified by compound number, against H. pylori with different strains.

| Strains | Compound 13 (µ/mL) | Compound 15 (µ/mL) | Compound 16 (µ/mL) | Compound 1 (µ/mL) |
|---|---|---|---|---|
| 49503 | 0.25-0.125 | 0.25 | 0.25-0.125 | 1.0-2.0 |
| 43504 | 0.5 | 1.0 | 1.0 | 2.0 |
| 51932 | 0.25-0.125 | 0.25 | 0.125-0.06 | 1.0 |

Example 5. Synergy of Exemplary Compounds with Secondary Agent

Compounds 1, 13, 15, and 16 were tested with Amoxxicillin, Clarithromycin, Omeprazole, and Pantoprazole. See FIG. 1.

Antibacterial synergy was tested using the checkerboard assay. The compound of interest was combined with antibiotics and proton pump inhibitors (PPIs). In this series of experiments cultures of H. pylori were adjusted to $OD_{600}=0.06$ and added to compound pairs that had been serially diluted in the same 96-well plates, vertically for one compound and horizontally for the other. Assays were carried out in triplicate as described in the antibacterial susceptibility assay sub-section. The combinatorial inhibitory concentration was indicated by the FICI.

$FICI = MIC_A$ combination$/MIC_A$ alone$+MIC_B$ combination$/MIC_B$ alone.

According to EUCAST (2000) a Synergistic effect ($Syn_E$) is observed when FICI value is ≤0.5; an Additive effect ($Add_E$) when 0.5<FICI value≤1; an Indifferent effect ($Ind_E$) when 1<FICI value<2 and an Antagonistic effect ($Ant_E$) when FICI value≥2.

Example 6. MIC in Acidic pH Environments

MIC data in acidic pH is shown in Table 6 for selected compounds identified by compound number.

TABLE 6

MIC data for exemplary compounds in acidic pH environments.

| pH | Compound 13 (µg/mL) | Compound 15 (µg/mL) | Compound 16 (µg/mL) | Compound 1 (µg/mL) |
|---|---|---|---|---|
| 7.0 | 0.25 | 0.25 | 0.25 | 1.0 |
| 6.5 | 0.25 | 0.25 | 0.25 | 1.0 |

TABLE 6-continued

MIC data for exemplary compounds in acidic pH environments.

| pH | Compound 13 (µg/mL) | Compound 15 (µg/mL) | Compound 16 (µg/mL) | Compound 1 (µg/mL) |
|---|---|---|---|---|
| 6.0 | 0.25 | 0.25 | 0.25 | 1.0 |
| 5.5 | 0.06 | 0.06 | 0.06 | 0.25 |

Example 7. Amount of Time to Kill *H. pylori*—Low Dose and High Dose of *H. pylori*

Figure 2:
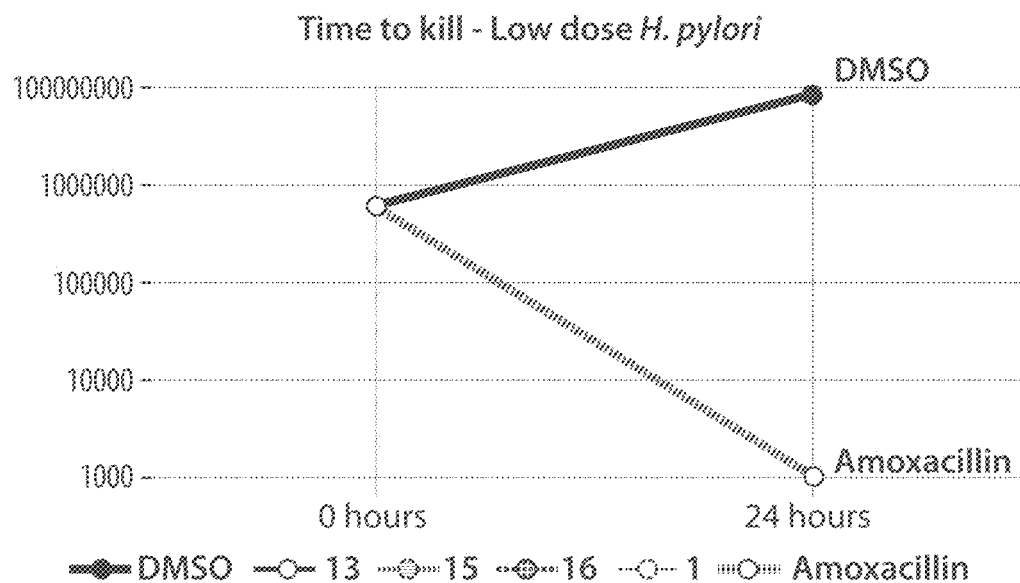
FIG. 2. shows the amount of time taken to kill low dose of *H. pylori* using compounds Compound 1, 13, 15, 16, and amoxacillin.

The time taken to kill low dose of *H. pylori* with using compounds 1, 13, 15, 16, and amoxacillin were measured. See FIG. 2.

Figure 3:
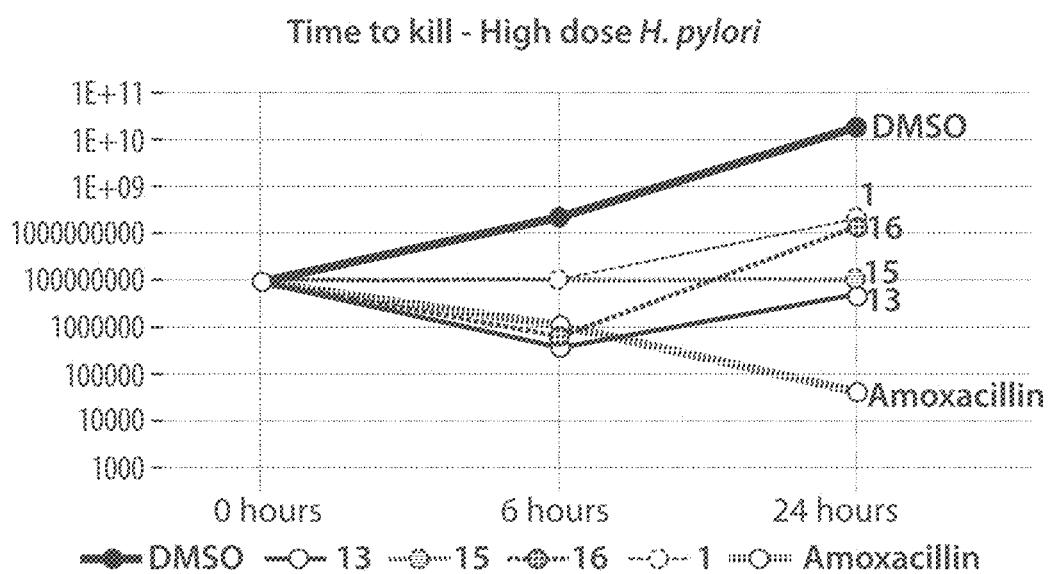
FIG. 3. shows the amount of time taken to kill high dose of *H. pylori* using compounds Compound 1, 13, 15, 16, and amoxacillin.

The time taken to kill high dose of *H. pylori* with using compounds 1, 13, 15, 16, and amoxacillin were measured. See FIG. 3.

The antibacterial properties of the compounds against *H. pylori* were examined using killing kinetic assays. Briefly, agar grown *H. pylori* bacteria were suspended in fresh MHB with 10% FBS to a density of 10' cells/mL and placed into 10 mL tubes (BD Biosciences). Test compounds were then added at the 4× MIC and incubated with agitation at 37° C. under microaerophilic conditions. Aliquots were periodically drawn from the tubes, serially diluted and plated onto *Brucella* agar (BD Biosciences) supplemented with 10% FBS. CFUs were counted after a 3-day incubation and assays were carried out in duplicate.

Example 8. Motility Measurements

Figure 4:
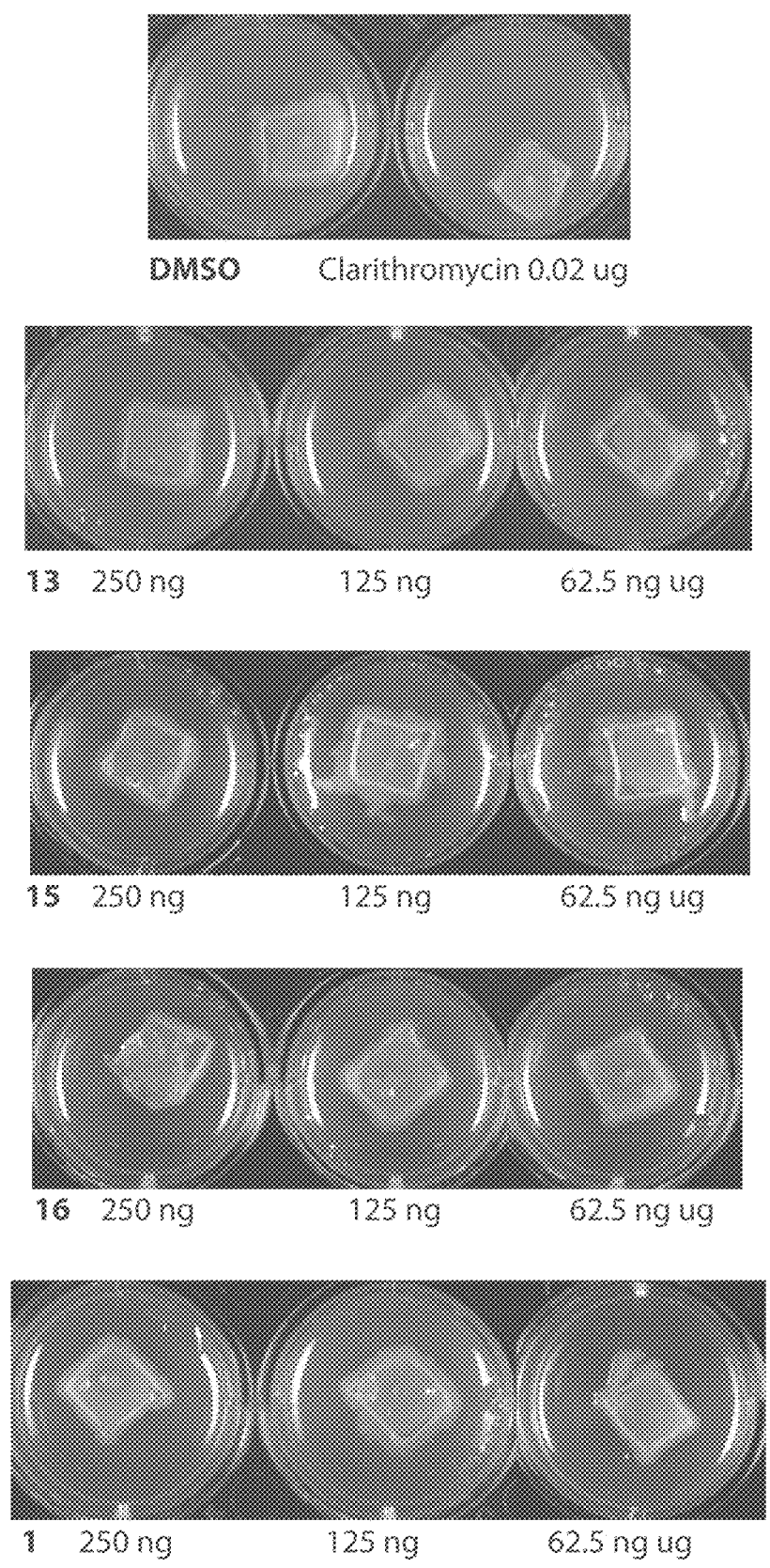
FIG. 4. shows motility of compounds 13, 15, 16, and Compound 1.

The motility of compounds 1, 13, 15, and 16 were measured as demonstrated by FIG. 4.

In brief, *Brucella* agar with 10% FBS was prepared in 2 layers. The bottom layer contained pre-casted 1.5% agar and the softer top layer was comprised of 0.4% agar and the compound (75, 100, 150 or 200 ng/mL). Agar-grown *H. pylori* cells were sliced and the densely grown *H. pylori* agar slice was placed facing up towards the soft layer and incubated as described in bacteria and mammalian cell culture subsection.

Example 9. Cytotoxicity

Figure 5:
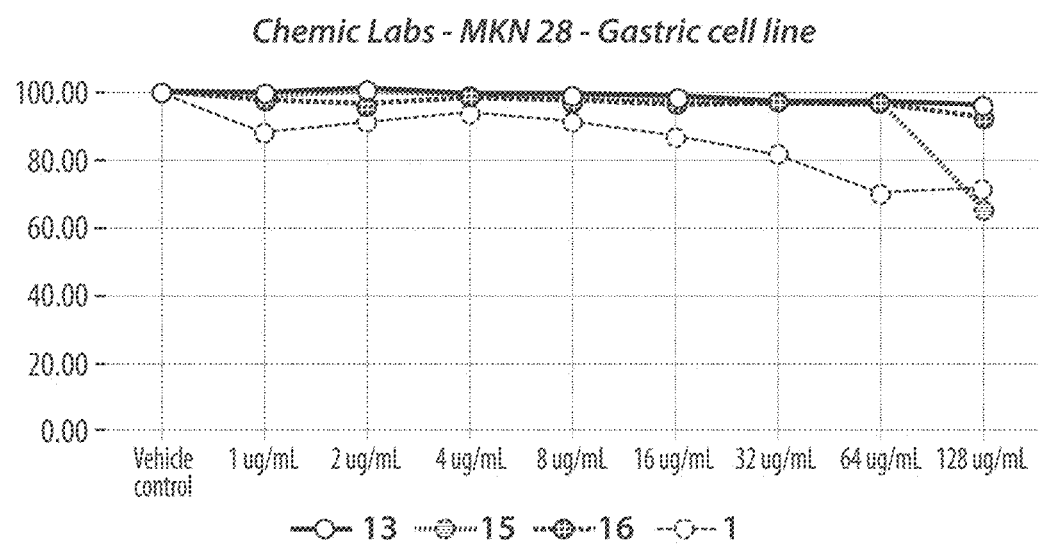
FIG. 5. shows cytotoxicity of different concentrations of compounds 13, 15, 16, and Compound 1 in MKN 28 gastric cell line.

Cytotoxicity of different concentrations of compounds 1, 13, 15, and 16 in an MKN 28-gastric cell line was measured. See FIG. 5.

Figure 6:
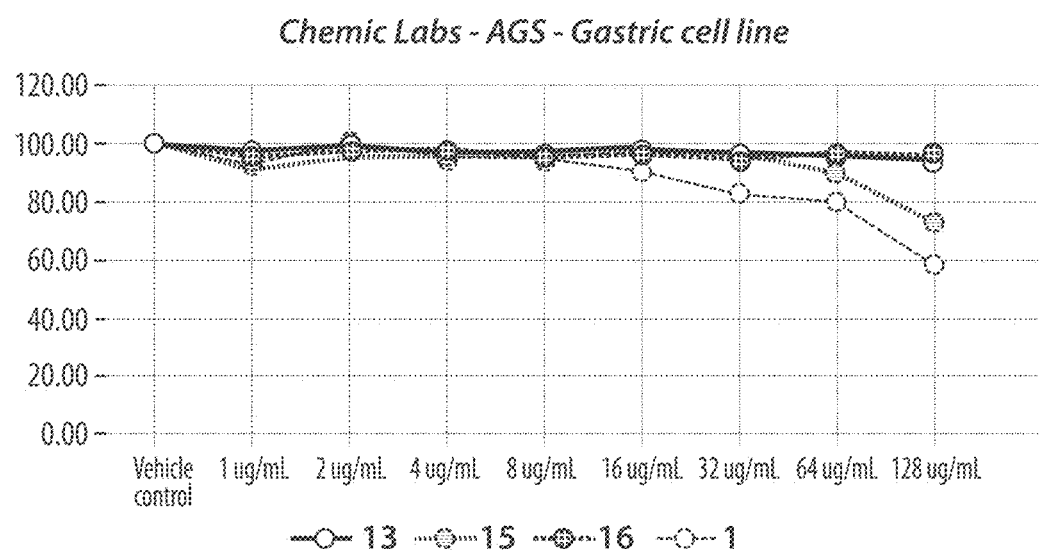
FIG. 6. shows cytotoxicity of different concentrations of compounds 13, 15, 16, and Compound 1 in AGS gastric cell line.

Cytotoxicity of different concentrations of compounds 1, 13, 15, and 16 in an AGS-gastric cell line was measured. See FIG. 6.

A procedure to measure the cytotoxicities is provided below:

HepG2 and AGS cells were used to test the cytotoxicity of the compounds. Cells were grown in DMEM (Gibco) supplemented with 10% fetal bovine serum (FBS) (Gibco) and 1% penicillin/streptomycin (Gibco) and maintained at 37° C. in 5% $CO_2$. $5 \times 10^4$ cells in 100 µL were added to wells of 96-well plates. Compounds were serially diluted in serum and antibiotic-free DMEM and added to the monolayer and incubated at 37° C. in 5% $CO_2$ for 24 h. At 4 h prior to the end of the incubation period, 10 µL of 2-(4-iodophenyl)-3-(4-nitrophenyl)-5-(2,4-disulfophenyl)-2H-tetrazolium (WST-1) solution (Roche, Mannheim, Germany) was added to each well. The WST-1 reduction was monitored at 450 nm using a Vmax microplate reader. Assays were performed in triplicate and the percentage survival was calculated by comparing the compound-treated wells to the DMSO-treated vehicle controls.

Example 10. *H. pylori* Adhesion to Gastric Epithelial Cells

Figure 7:
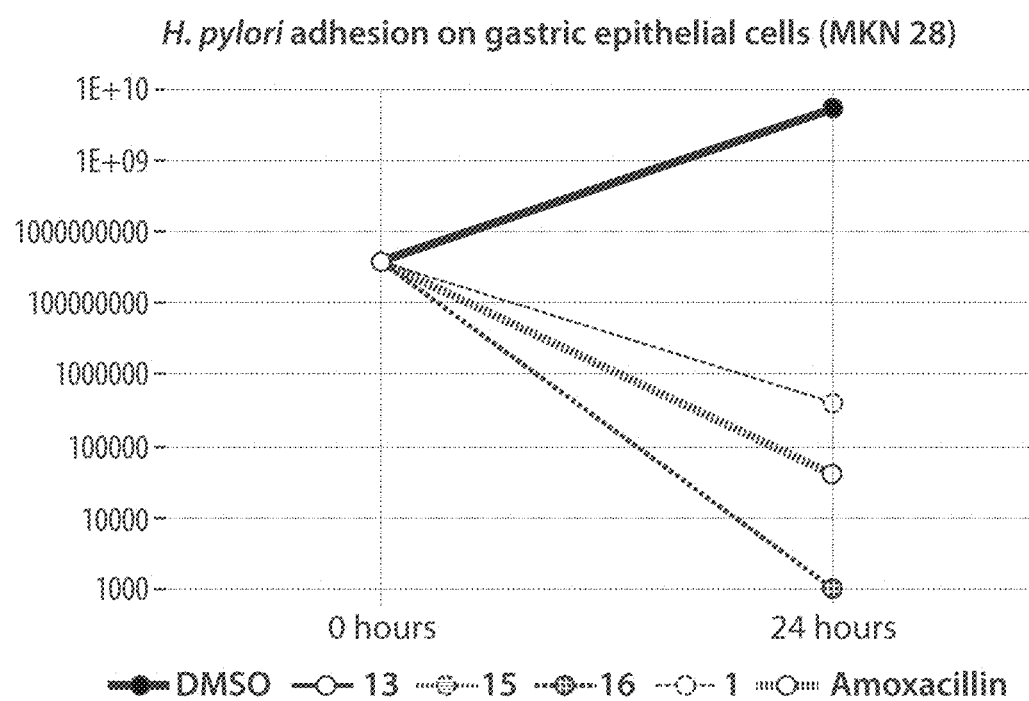
FIG. 7. shows *H. pylori* adhesion to gastric epithelial cells at different time points.

*H. pylori* adhesion to gastric epithelial cells were measured at different time points. See FIG. 7. A procedure for measuring this adhesion is provided below:

The AGS (Gastric adenocarcinoma cell lines) cell line was used to examine inhibition of adhesion and invasion of *H. pylori* by the compound of interest. The AGS cells were grown in DMEM (Gibco), supplemented with 10% fetal bovine serum (FBS) (Gibco) and 1% penicillin/streptomycin (Gibco) and maintained at 37° C. in 5% $CO_2$. Then, $5 \times 10^5$ cells in antibiotic and serum-free DMEM were seeded in 6-well plates 24 h prior to infection. *H. pylori* bacteria at a multiplicity of infection (MOI)=100 were added and allowed to adhere to the surface of the AGS cells. Planktonic bacteria were removed after 2 h and DMEM with the compound (1×MIC) was then added to the wells containing the AGS. The mammalian cells were lysed by 0.1% saponin after 20 h of incubation and the adhered bacteria were then serially diluted, plated in *Brucella* agar supplemented with 10% FBS, and incubated as described earlier. To determine the bacterial invasion inhibition, AGS cells were treated with DMEM supplemented with 200 µg/mL gentamicin and incubated for 1.30 h to eliminate extracellular bacteria. Antibiotic and serum-free DMEM with and without test compounds were added and incubated in 5% $CO_2$ for 20 h. Cell lysate preparation, plating, and incubation were carried out as we described in the adhesion assay. Assays were carried out in triplicate.

Example 11. Vacuolation Inhibition

Figure 8:
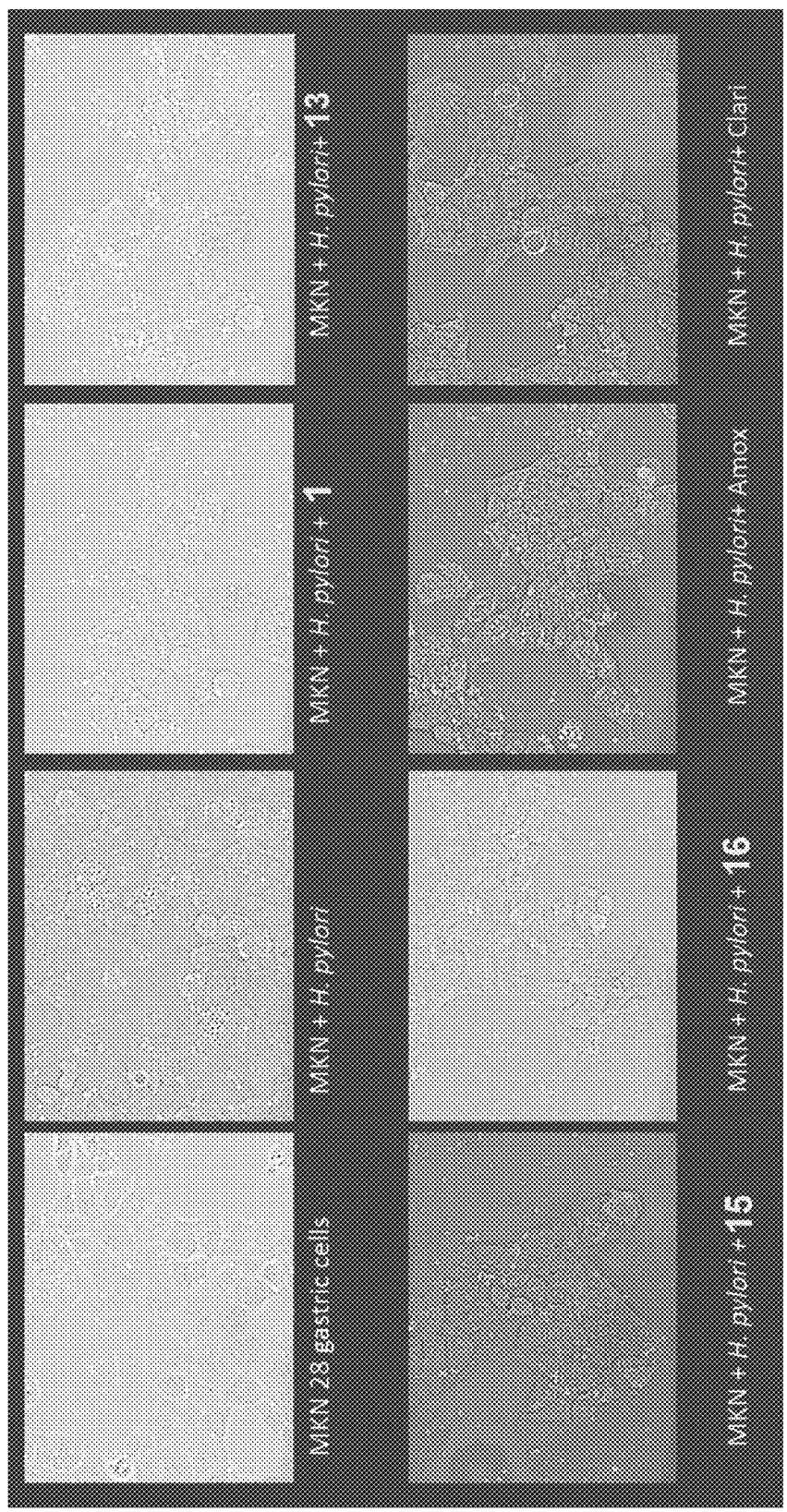
FIG. 8. shows vacuolation inhibition of compounds 13, 15, 16, and Compound 1 against *H. pylori* and MKN.
Figure 9:
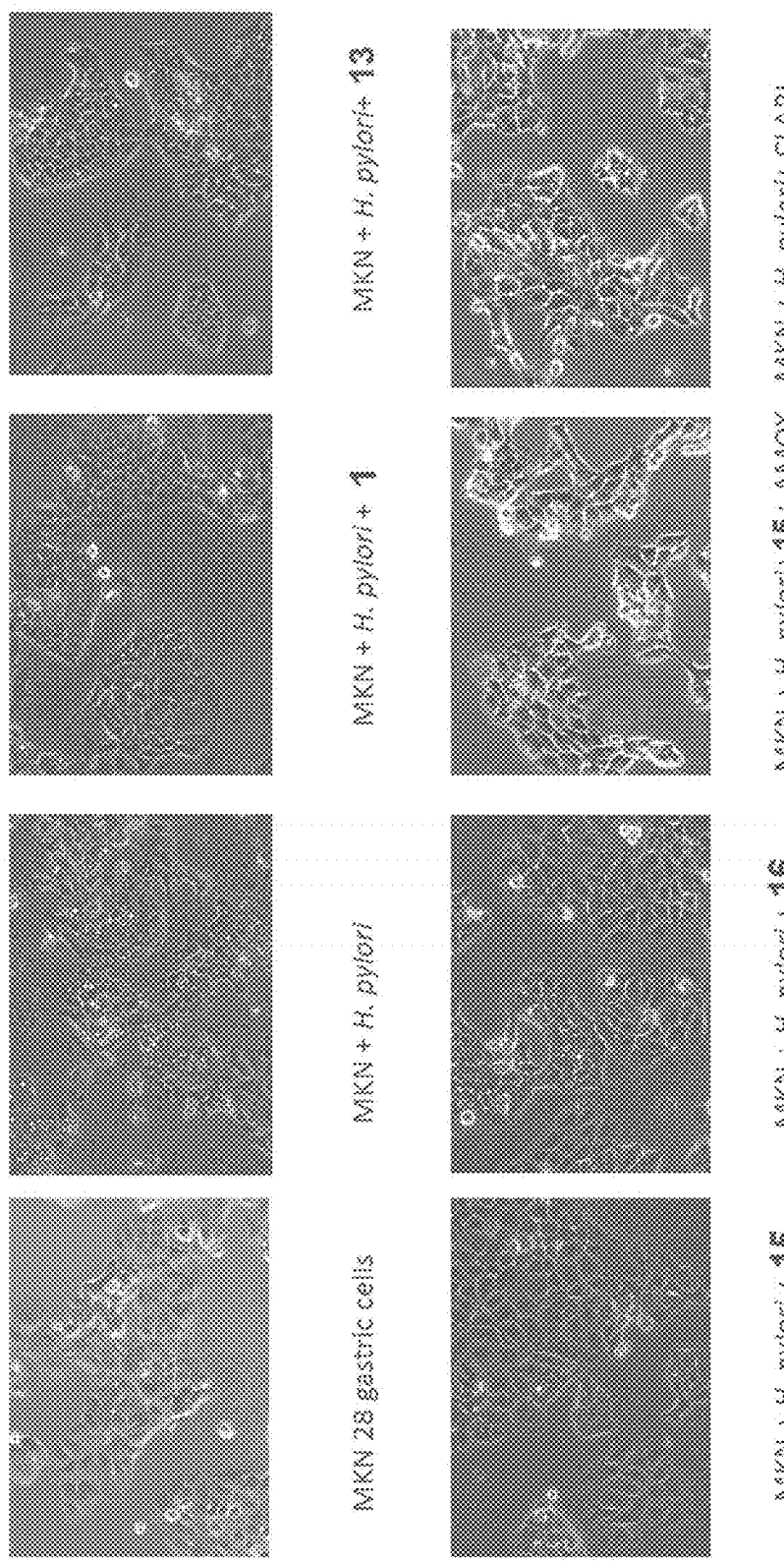
FIG. 9. shows an additional representation vacuolation inhibition of compounds 13, 15, 16, and Compound 1 against *H. pylori* and MKN.

Vacuolation inhibition of compounds 1, 13, 15, and 16 were measured against *H. pylori* and MKN. See FIGS. 8 and 9. A procedure to measure vacuolation inhibition is provided below:

*H. pylori* bacteria secrete VacA toxin via a type V secretion system. This toxin binds to host gastric epithelial cells and its internalization leads to vacuolation, characterized by the accumulation of large vacuoles in gastric epithelial cells during the infection process. AGS cells were harvested and seeded into a 6 well plate at a concentration of $5 \times 10^5$ cells, 24 h before experimentation. *H. pylori* bacteria were harvested and washed with sterile PBS and co-cultured with AGS at a MOI of 100. After incubation for 24 h, the cells were washed, magnified under a microscope, and examined for vacuolation.

Example 12. Insect Survival

Figure 10:
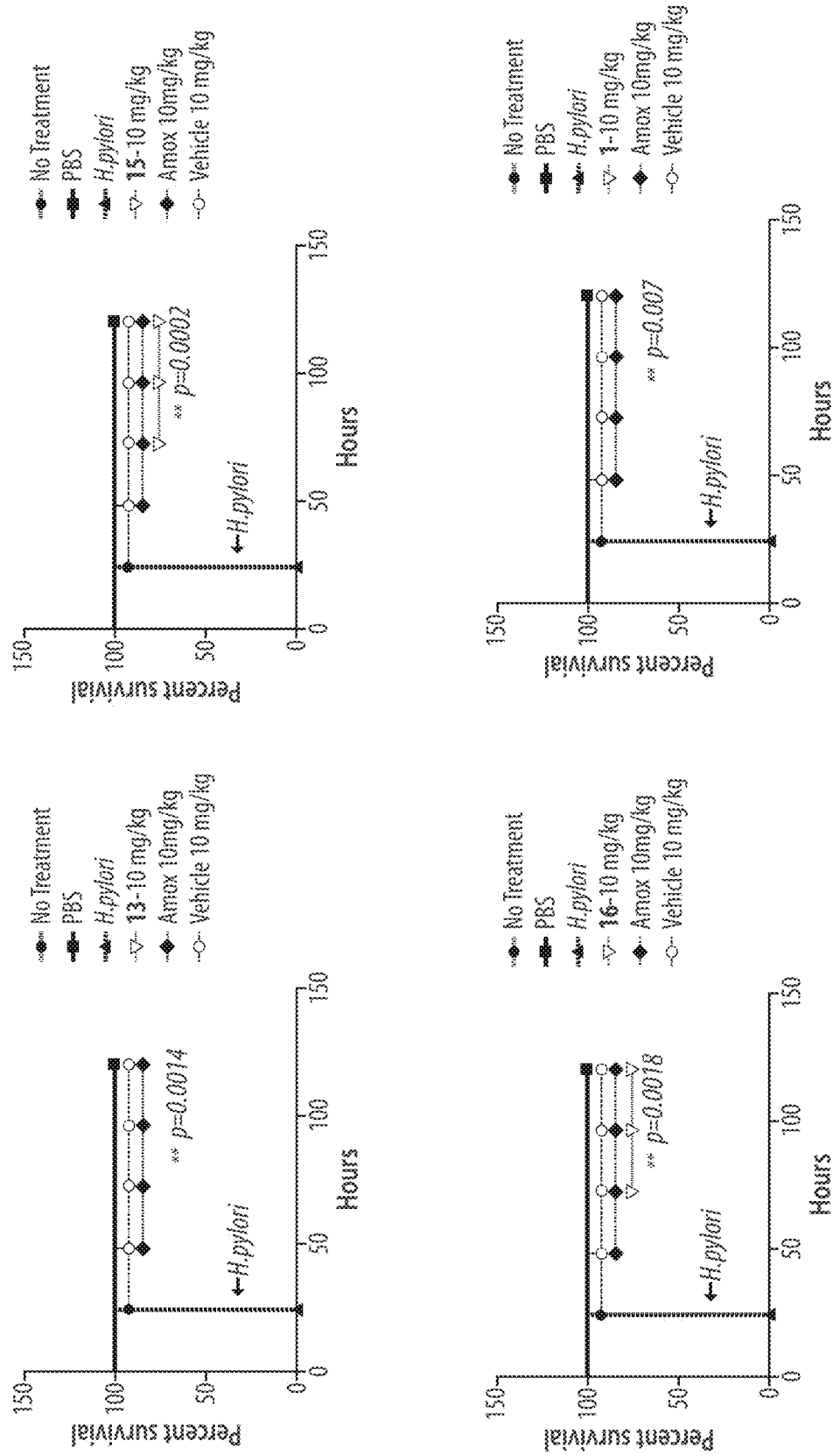
FIG. 10. shows the percentage of insects surviving the treatment of compounds 13, 15, 16, and Compound 1 at different time points.

The percentage of insects surviving the treatment of compounds 1, 13, 15, and 16 at different time points were measured. See FIG. 10. An exemplary procedure to assess insect survival is provided below:

Twelve randomly selected *G. mellonella* larvae 300-350 mg was used for each group in the experiment. *H. pylori* cells were washed with PBS and diluted to $OD_{600}$=0.3, before inoculation into *G. mellonella* larvae. A 10 µL inoculum was injected into the last left proleg using a 10 µL Hamilton syringe. After 2 h, compounds were administered at into the last right proleg and the wax moths were incubated at 37° C. Three control groups—(1) injected with PBS only, (2) inoculated with *H. pylori* but treated with sham injections, (3) no manipulation—were included. *G. mellonella* survival was evaluated up to 120 h and considered dead if unresponsive to touch. Killing curves and differences in survival were analyzed by the Kaplan-Meier method using GraphPad Prism version 6.04 (GraphPad Software, La Jolla, CA, USA). Statistical analysis (Kruskal-Wallis test) was carried out using the same program.

OTHER EMBODIMENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (IV):

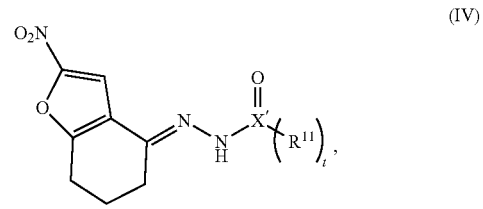

or pharmaceutically acceptable salt thereof, wherein:

X' is carbon or phosphorus;

$R^{11}$ is each and independently selected from the group consisting of substituted or unsubsistuted $C_{1-6}$ alkyl, substituted or unsubstituted $C_{1-6}$ alkoxy, —$NHC_{1-6}$ alkyl, —$NHC_6H_5$, and $C_{2-6}$ alkenyl, wherein the alkenyl is optionally substituted with substituted or unsubstituted 5-7 membered aryl; and t is 1 or 2, wherein t is 1 when X' is carbon; and when X' is phosphorous t is 2.

2. The compound of claim 1, wherein X' is carbon and t is 1.

3. The compound of claim 1, wherein X' is phosphorus and t is 2.

4. The compound of claim 1, wherein $R^{11}$ is $C_{2-6}$ alkenyl, wherein the alkenyl is optionally substituted with substituted or unsubstituted 5-7 membered aryl.

5. The compound of claim 1, wherein the compound is selected from the group consisting of:

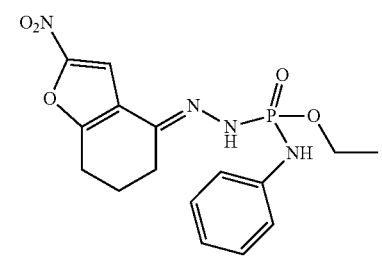

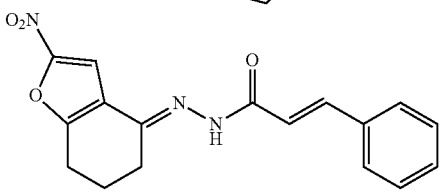

-continued

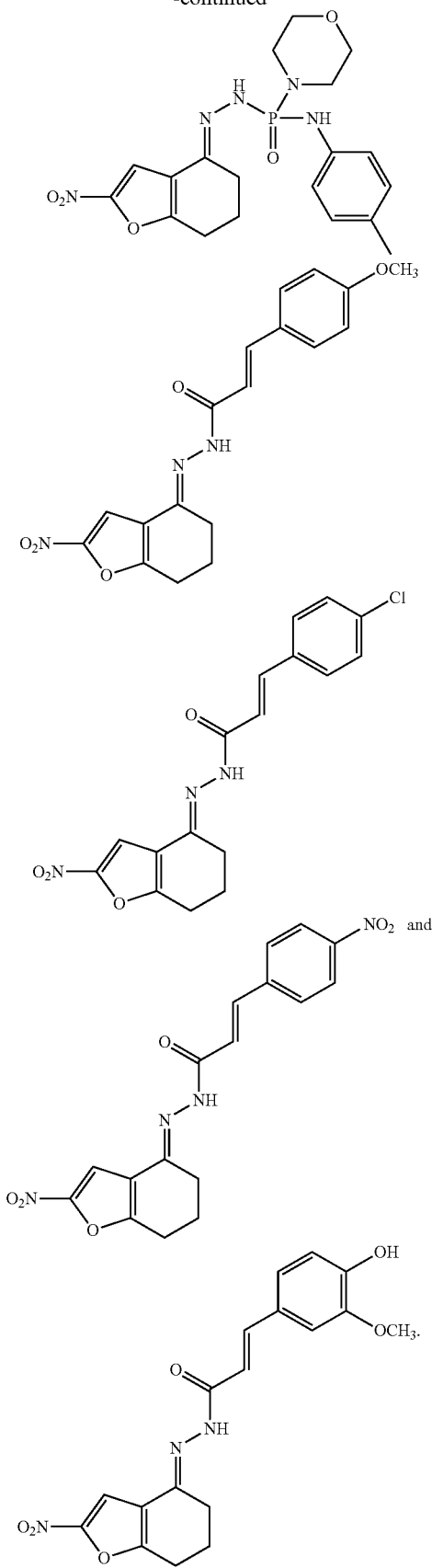

6. A method of treating or ameliorating a gastrointestinal infection caused by *H. pylori* in a patient in need thereof, comprising administering to the patient the compound of claim 1 or pharmaceutically acceptable salt thereof.

7. A method of treating or ameliorating a gastrointestinal infection caused by *H. pylori* in a patient in need thereof, comprising administering to the patient:

(i) an effective amount of a compound of Formula (IV):

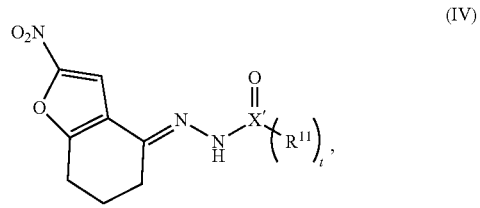

(IV)

or pharmaceutically acceptable salt thereof, wherein:

X' is carbon or phosphorus;

$R^{11}$ is each and independently selected from the group consisting of substituted or unsubsistuted $C_{1-6}$ alkyl, substituted or unsubstituted $C_{1-6}$ alkoxy, —$NHC_{1-6}$ alkyl, —$NHC_6H_5$, and $C_{2-6}$ alkenyl, wherein the alkenyl is optionally substituted with substituted or unsubstituted 5-7 membered aryl; and t is 1 or 2, wherein t is 1 when X' is carbon; and when X' is phosphorous t is 2; and (ii) and an effective amount of an additional agent.

8. The method of claim 7, wherein the additional agent is an acid suppressor.

9. The method of claim 8, wherein the acid suppressor is selected from the group consisting of omeprazole, pantoprazole, lansoprazole, dexlasoprazole, rabeprazole, ranitidine bismuth citrate, and bismuth subsalicylate, and esomeprazole.

10. The method of claim 7, wherein the compound is selected from the group consisting of:

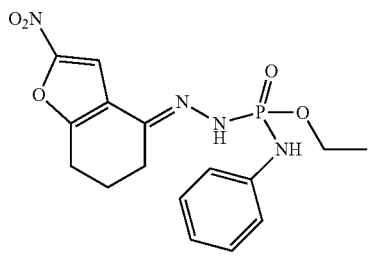

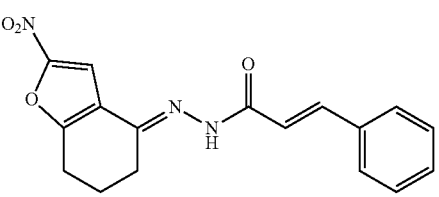

-continued
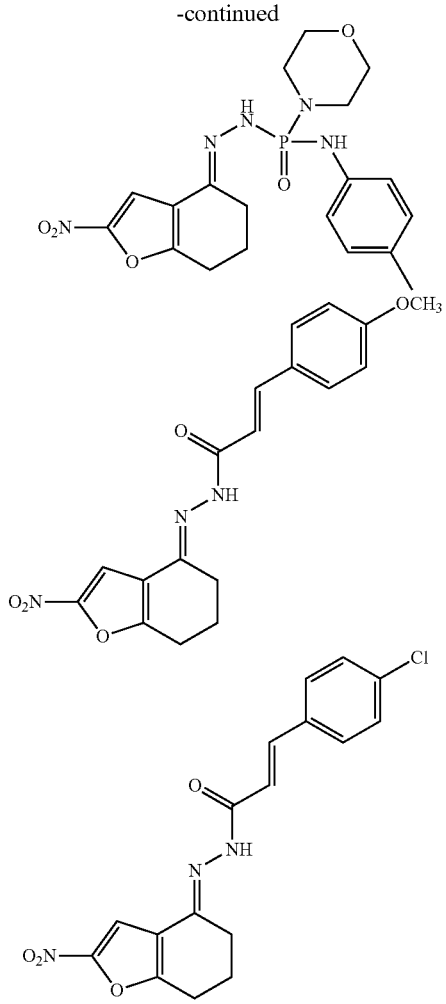
-continued
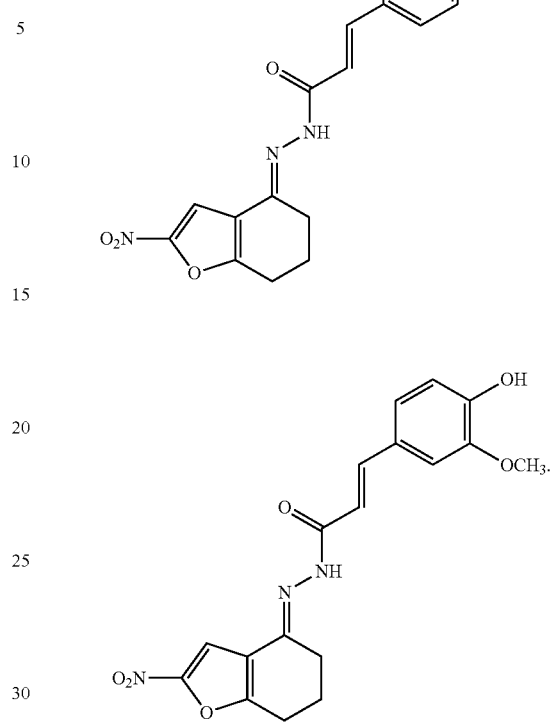
11. The method of claim 7, wherein the gastrointestinal infection is gastric mucosal inflammation.
12. The method of claim 8, wherein the acid suppressor is selected from the group consisting of lansoprazole, esomeprazole, and rabeprazole.
* * * * *